United States Patent [19]

Green

[11] Patent Number: 4,568,009
[45] Date of Patent: Feb. 4, 1986

[54] SURGICAL FASTENER APPLYING APPARATUS

[75] Inventor: David T. Green, Norwalk, Conn.

[73] Assignee: United States Surgical Corporation, Norwalk, Conn.

[21] Appl. No.: 598,461

[22] Filed: Apr. 9, 1984

Related U.S. Application Data

[63] Continuation-in-part of Ser. No. 572,659, Jan. 20, 1984, abandoned, which is a continuation-in-part of Ser. No. 538,931, Oct. 4, 1983, Pat. No. 4,508,253.

[51] Int. Cl.[4] ............................................. A61B 17/00
[52] U.S. Cl. .................. 227/19; 128/334 R; 227/DIG. 1
[58] Field of Search ............... 128/334 R, 334 C; 227/19, 120, 135, 142, 156, DIG. 1

[56] References Cited

U.S. PATENT DOCUMENTS

| | | | |
|---|---|---|---|
| 3,080,564 | 3/1963 | Strekopitov et al. | 227/19 |
| 3,269,630 | 8/1966 | Fleischer | 227/107 |
| 3,275,211 | 9/1966 | Hirsch et al. | 227/124 |
| 3,315,863 | 4/1967 | O'Dea | 227/19 |
| 3,494,533 | 2/1970 | Green et al. | 227/19 |
| 3,589,589 | 6/1971 | Akopov | 227/153 |
| 3,692,224 | 9/1972 | Astafiev et al. | 227/19 |
| 3,935,981 | 2/1976 | Akopov et al. | 227/19 |
| 3,949,923 | 4/1976 | Akopov et al. | 227/19 |
| 4,241,861 | 12/1980 | Fleischer | 227/135 |
| 4,296,881 | 10/1981 | Lee | 227/30 |
| 4,305,539 | 12/1981 | Korolkov et al. | 227/8 |
| 4,351,466 | 9/1982 | Noiles | 227/8 |
| 4,354,628 | 10/1982 | Green | 227/19 |
| 4,383,634 | 5/1983 | Green | 227/19 |
| 4,402,444 | 9/1983 | Green | 227/19 |
| 4,429,695 | 2/1984 | Green | 128/305 |

FOREIGN PATENT DOCUMENTS 906791 9/1962 United Kingdom .
913218 12/1982 United Kingdom .

*Primary Examiner*—Paul A. Bell
*Attorney, Agent, or Firm*—Robert R. Jackson; John E. Nathan

[57] ABSTRACT

Surgical fastener applying apparatus including an actuator and a removable surgical fastener containing cartridge. The cartridge fits loosely into a cartridge holder part of the actuator which translates linearly toward or away from an anvil part of the actuator. As the cartridge holder translates toward the anvil, the cartridge is automatically brought into alignment and registration with the anvil.

19 Claims, 30 Drawing Figures

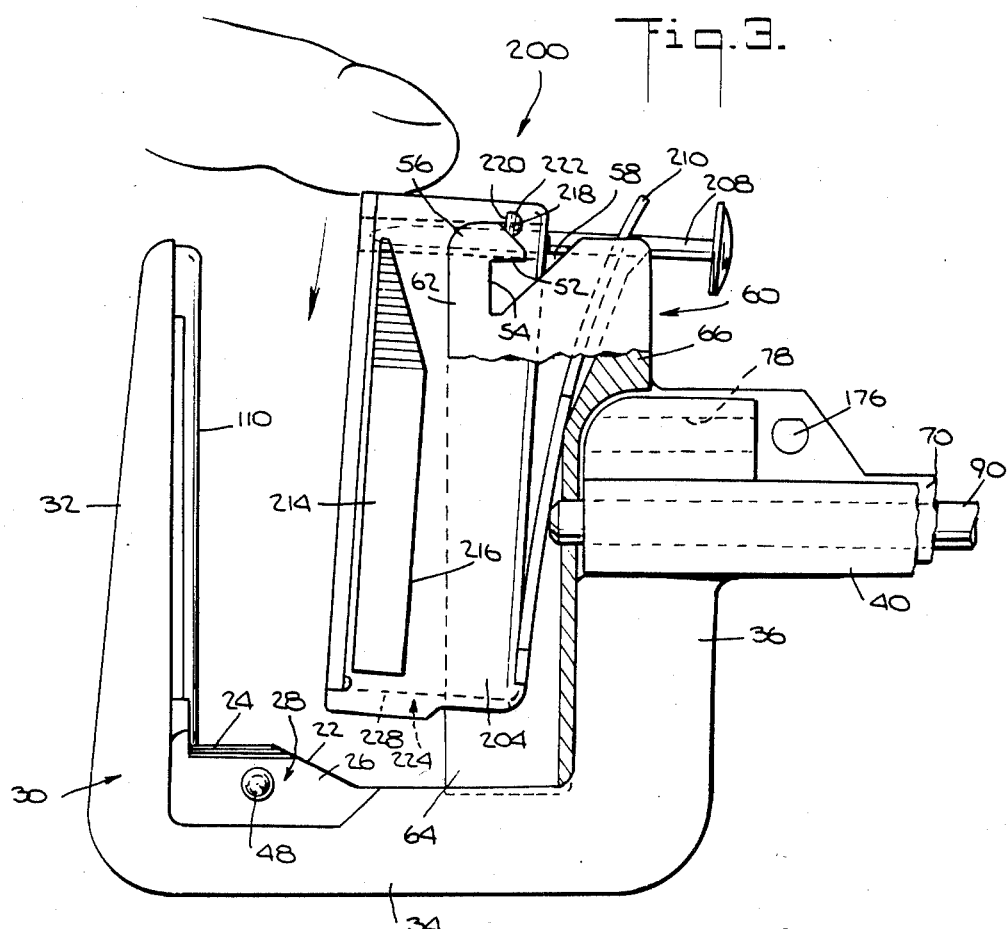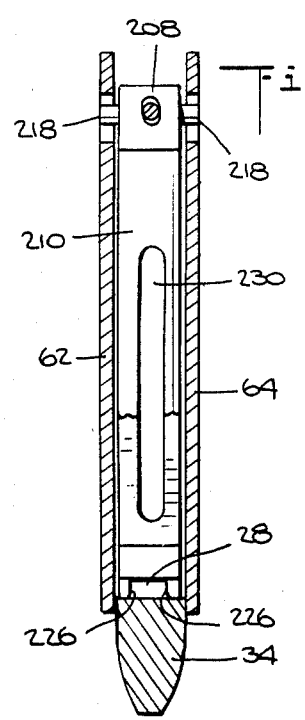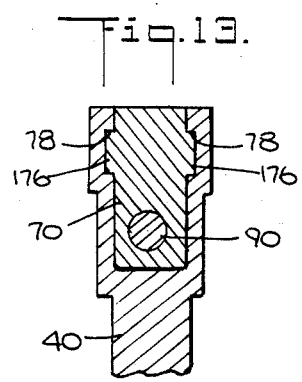

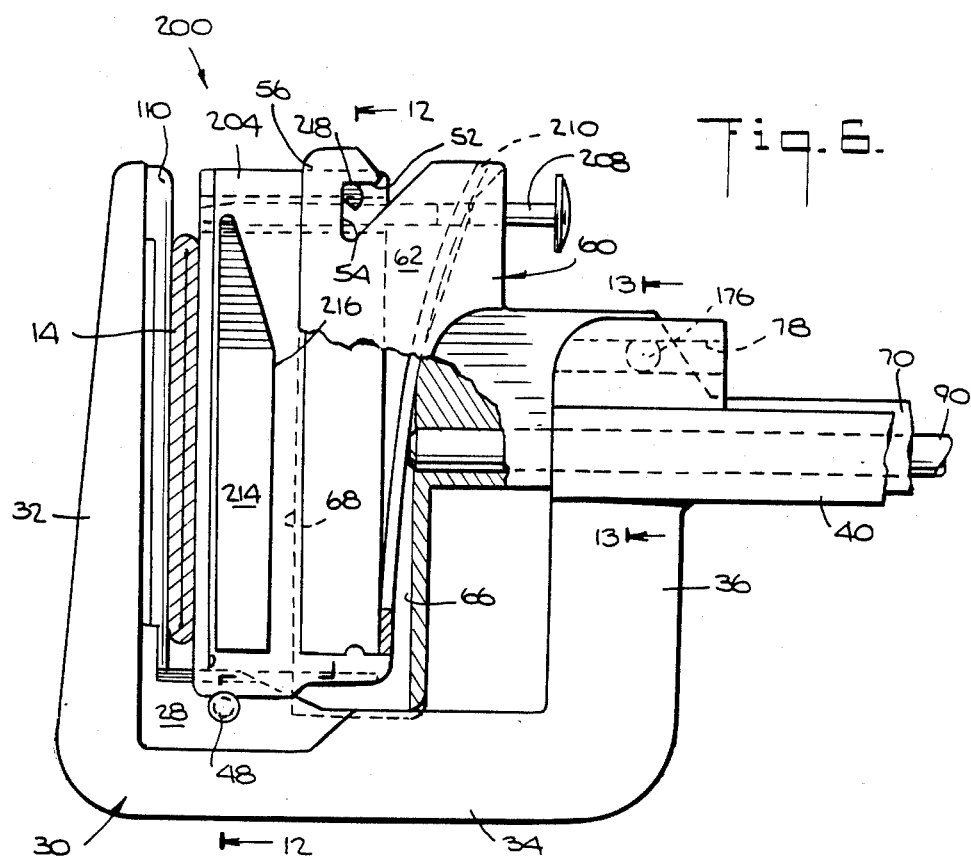
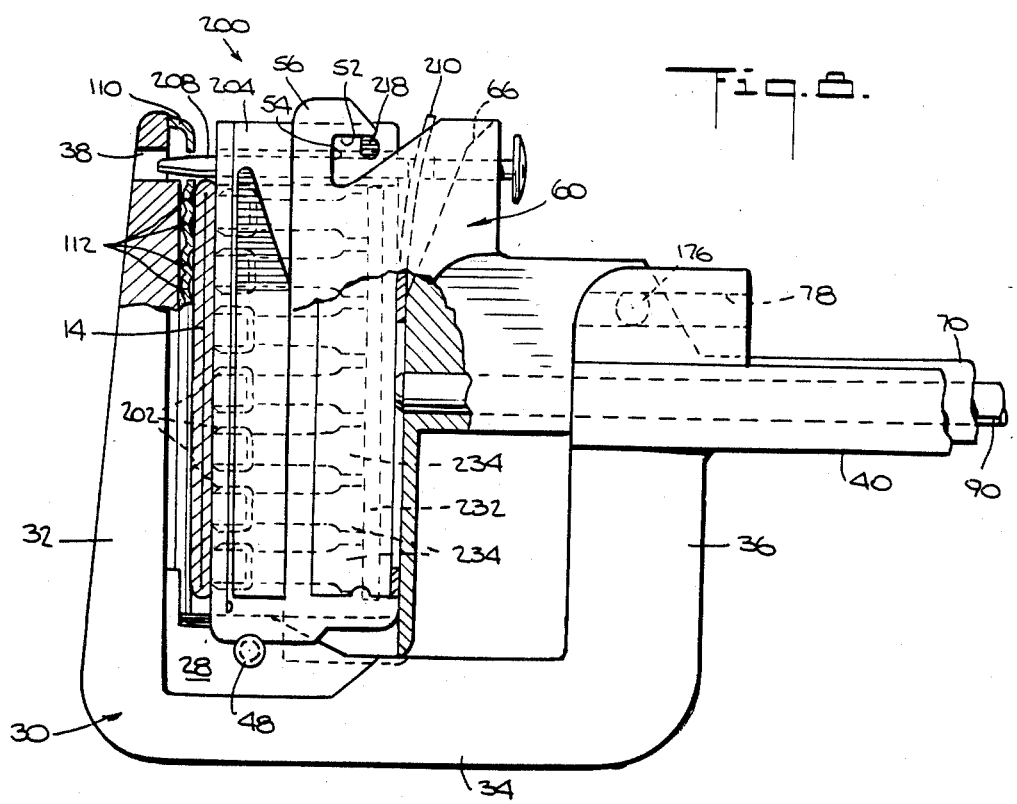

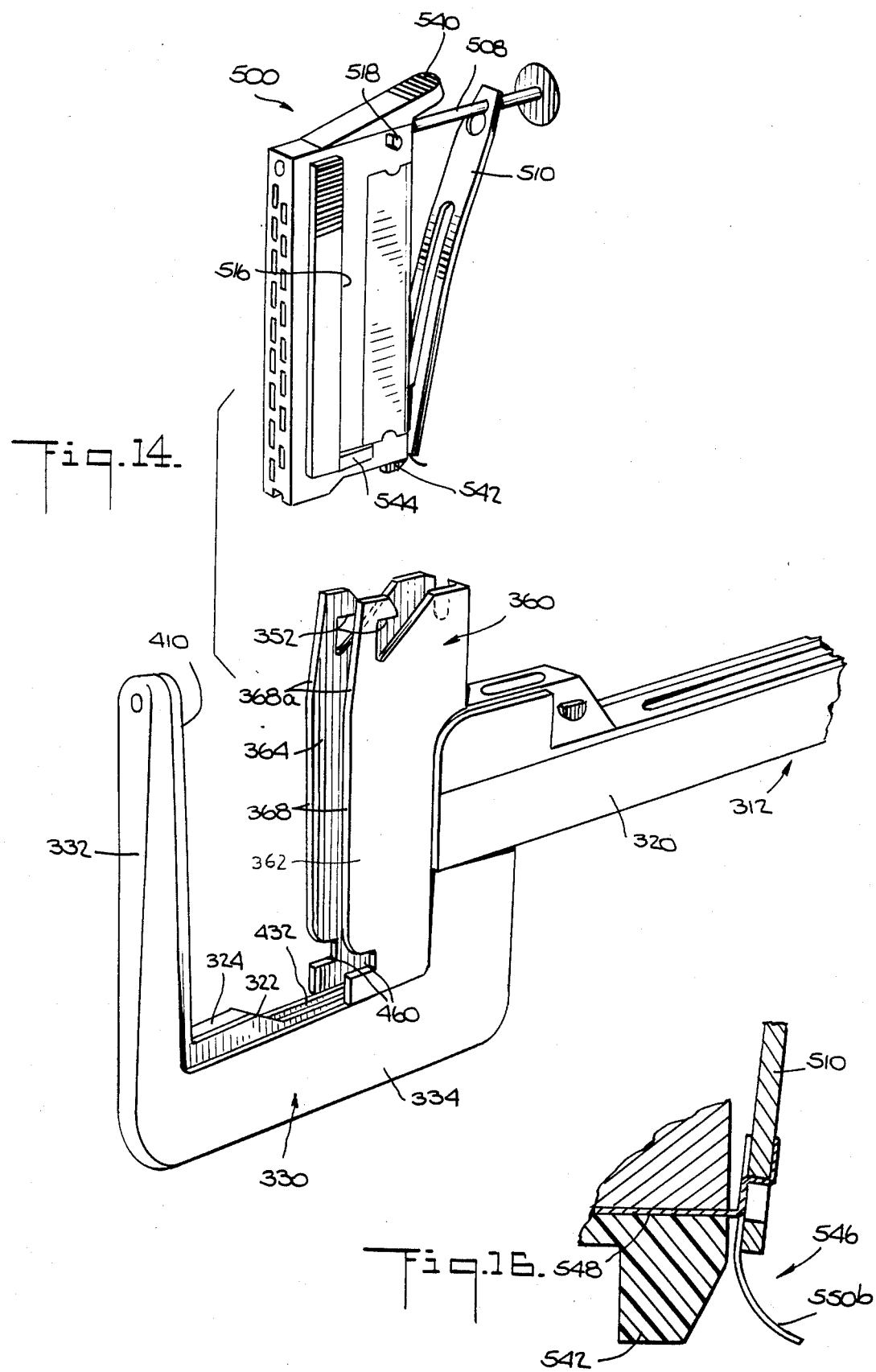

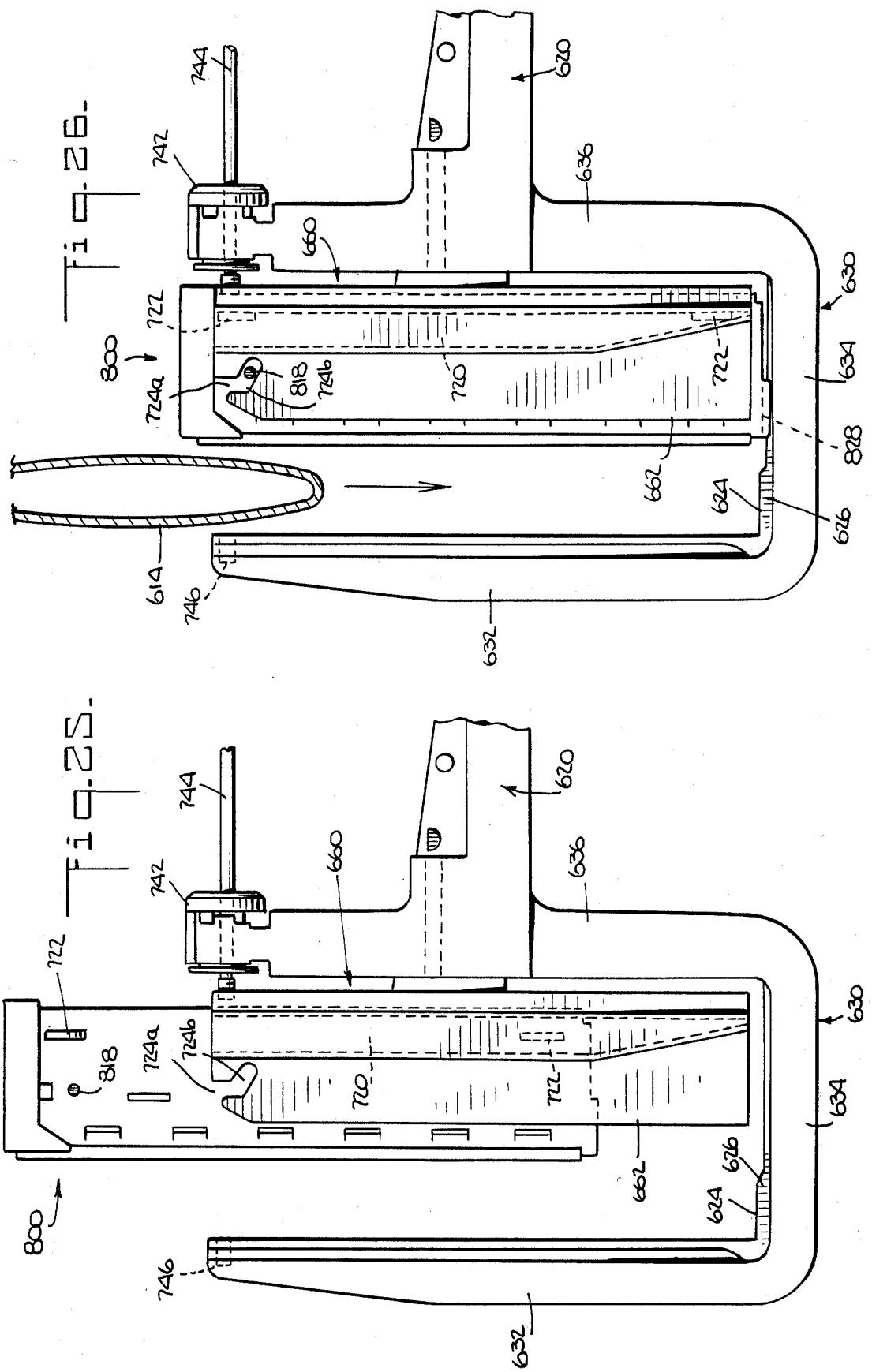

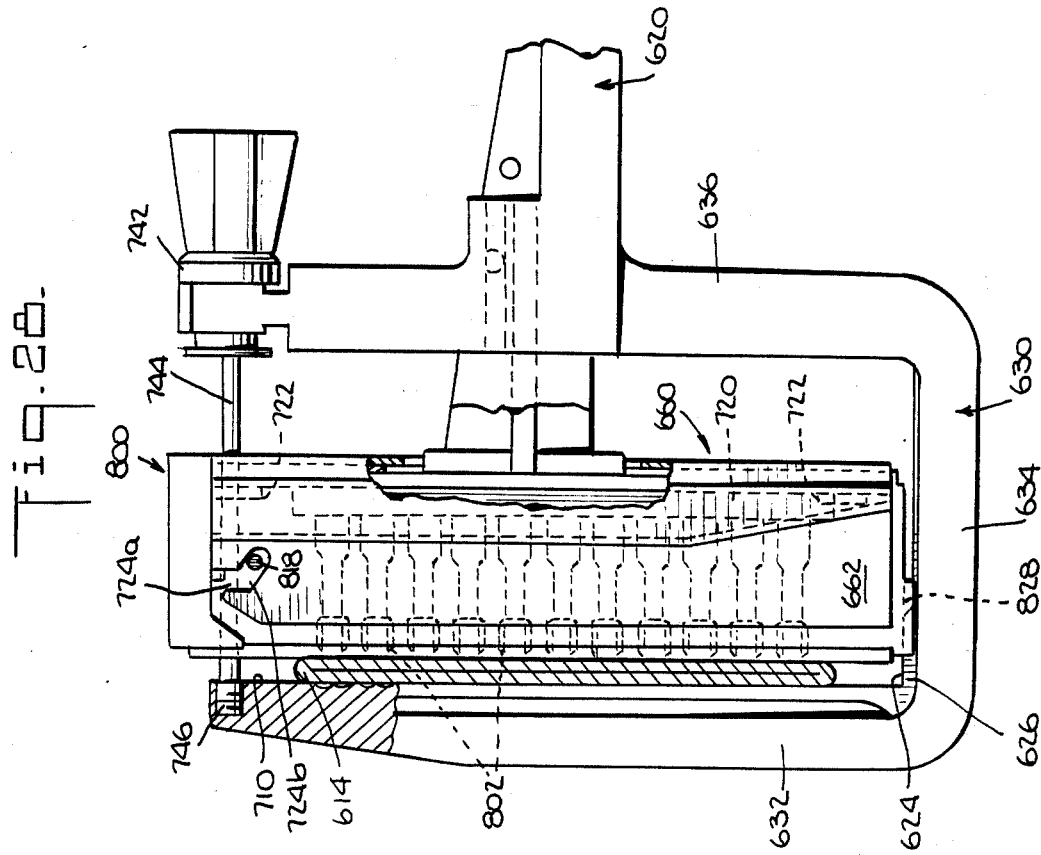
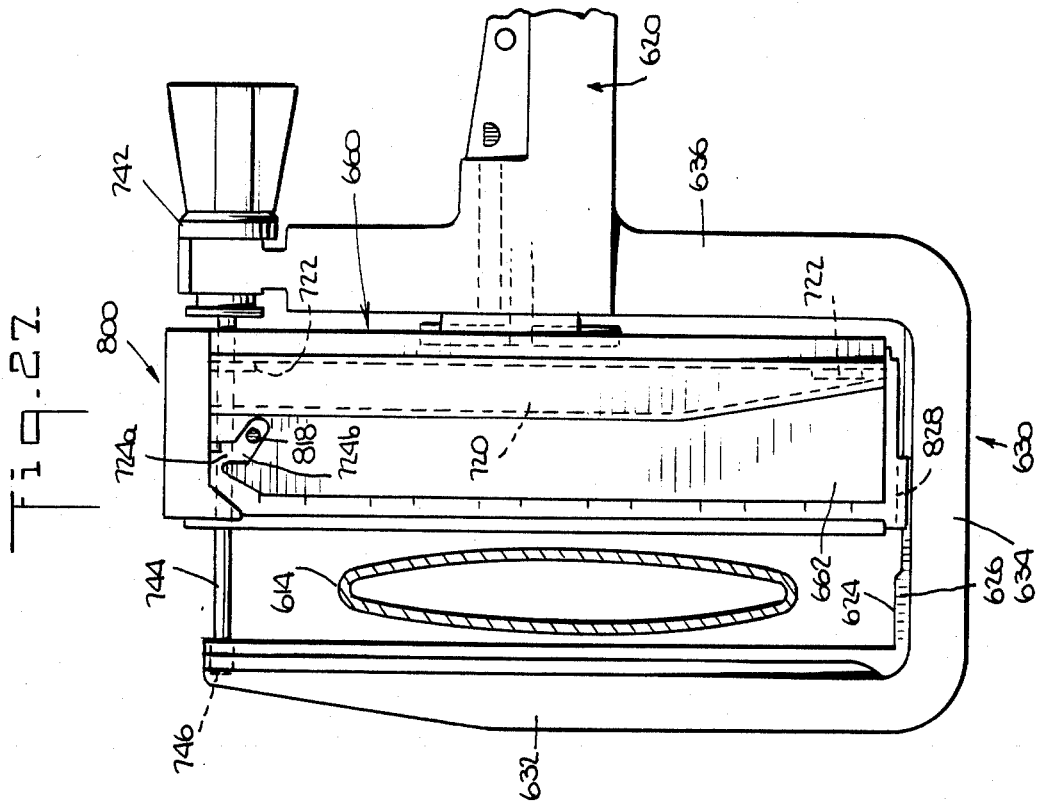

4,568,009

SURGICAL FASTENER APPLYING APPARATUS

This is a continuation-in-part of U.S. patent application Ser. No. 572,659, filed Jan. 20, 1984, now abandoned, which is a continuation-in-part of U.S. patent application Ser. No. 538,931, filed Oct. 4, 1983, U.S. Pat. No. 4,508,253.

FIELD OF THE INVENTION

This invention relates to apparatus for applying surgical fasteners such as metal surgical staples. More particularly, the invention relates to surgical fastener applying apparatus of the type which includes an actuator for removably receiving a fastener containing cartridge.

BACKGROUND OF THE INVENTION

There are several types of known surgical fastener applying devices which comprise an actuator for removably receiving a fastener containing cartridge. One such device is shown in Hirsch et al. U.S. Pat. No. 3,275,211. In the Hirsch et al. device, a cartridge containing a plurality of surgical staples fits snugly into a cartridge holder element of the actuator. The cartridge holder element reciprocates linearly toward or away from an anvil portion of the actuator by operation of a first actuator control element (i.e., a rotating knob or wing nut). In particular, the tissue to be fastened is clamped between the cartridge and the anvil by reciprocating the cartridge holder element (and therefore the cartridge) toward the anvil. The staples are driven from the cartridge and part way through the clamped tissue by operation of a second actuator control element (i.e., a pivoting handle). The ends of the staple legs are crimped or clinched by contact with the anvil.

The Hirsch et al. device has many desirable features, but satisfactory operation of that device depends on accurate alignment between the cartridge and the anvil in order to assure that all of the staple legs enter the staple clinching pockets in the anvil for proper clinching by the anvil. Thus the cartridge must fit snugly in the cartridge holder element, and the cartridge holder element must be precisely aligned with the anvil, while at the same time being movable relative to the anvil and capable of resisting the large tissue clamping and staple clinching forces which tend to drive the staple holder and anvil apart.

Some of the requirements of the Hirsch et al. device are alleviated by devices of the type shown in Green U.S. Pat. No. 4,383,634. In the Green device the staple holder, anvil, and alignment pin are all connected together in a single disposable unit. In addition, the alignment pin operates automatically when the actuator is operated. The elements which provide the necessary precise alignment between the staple holder and anvil are also all confined to the cartridge assembly, thereby greatly simplifying and reducing the cost of the actuator. However, in the Green device, the staple holder and anvil are pivotally connected to one another (although limited translational motion of these elements is also possible). Some users prefer the purely linear reciprocation of the staple holder relative to the anvil which is characteristic of the Hirsch et al. device.

In view of the foregoing, it is an object of this invention to improve and simplify surgical fastener applying apparatus of the type described above.

It is a more particular object of this invention to provide surgical fastener applying apparatus which combines the relatively low cost construction and simplified operation of the above-mentioned Green device with the linear relative motion of the staple holder and anvil in the above-mentioned Hirsch et al. device.

SUMMARY OF THE INVENTION

These and other objects of the invention are accomplished in accordance with the principles of the invention by providing a staple holding cartridge which drops relatively loosely into a cartridge holder part of an actuator. The cartridge drops into the cartridge holder at an angle relative to the anvil, and means are provided for urging the cartridge into substantial parallelism with the anvil after the cartridge is in the holder. Means are also provided for retaining the cartridge in the holder when the cartridge is substantially parallel to the anvil.

The cartridge holder reciprocates linearly relative to the anvil. One end of the staple holding cartridge is aligned relative to the anvil by means of a rail and channel connection between the cartridge and the actuator member which terminates in the anvil. Reciprocation of the cartridge holder toward the anvil automatically forces the cartridge into parallel alignment with the anvil. As the cartridge becomes parallel to the anvil, means associated with the cartridge and cartridge holder force the elements of the rail and channel connection together, thereby assuring proper registration of the cartridge with the anvil in a direction parallel to the longitudinal axis of the anvil.

The cartridge also includes an alignment pin adjacent the end remote from the rail and channel connection. When the cartridge holder is reciprocated toward the anvil, the alignment pin automatically extends from the cartridge into the anvil, thereby assuring proper alignment of the end of the cartridge and anvil remote from the rail and channel connection.

Further features of the invention, its nature and various advantages will be more apparent from the accompanying drawing and the following detailed description of the invention.

BRIEF DESCRIPTION OF THE DRAWING

FIG. 3 is a partly sectional elevational view of a part of the apparatus of FIG. 1 showing a later stage in the operation of that apparatus.

FIGS. 4-6 are views generally similar to FIG. 3 showing successive further stages in the operation of the apparatus of FIG. 1.

FIG. 7 is a view generally similar to FIG. 2 showing a still later stage in the operation of the apparatus of FIG. 1.

FIG. 8 is a view generally similar to FIGS. 3-6 showing the same condition of the FIG. 1 apparatus as is shown in FIG. 7.

FIG. 11 is a sectional view taken along the line 11—11 in FIG. 4.

FIGS. 12 and 13 are sectional views taken along the lines 12—12 and 13—13, respectively, in FIG. 6.

FIG. 14 is a partial perspective view of a second illustrative embodiment of the invention showing the fastener holding cartridge and the cartridge actuator separate from one another.

FIG. 16 is a sectional view taken along the line 16—16 of FIG. 15.

FIG. 25 is an elevational view of the apparatus of FIG. 24.

FIGS. 26-30 are views generally similar to FIG. 25 showing successive stages in the operation of the apparatus of FIG. 24.

DETAILED DESCRIPTION OF THE INVENTION

I. First Illustrative Embodiment

Figure 1:
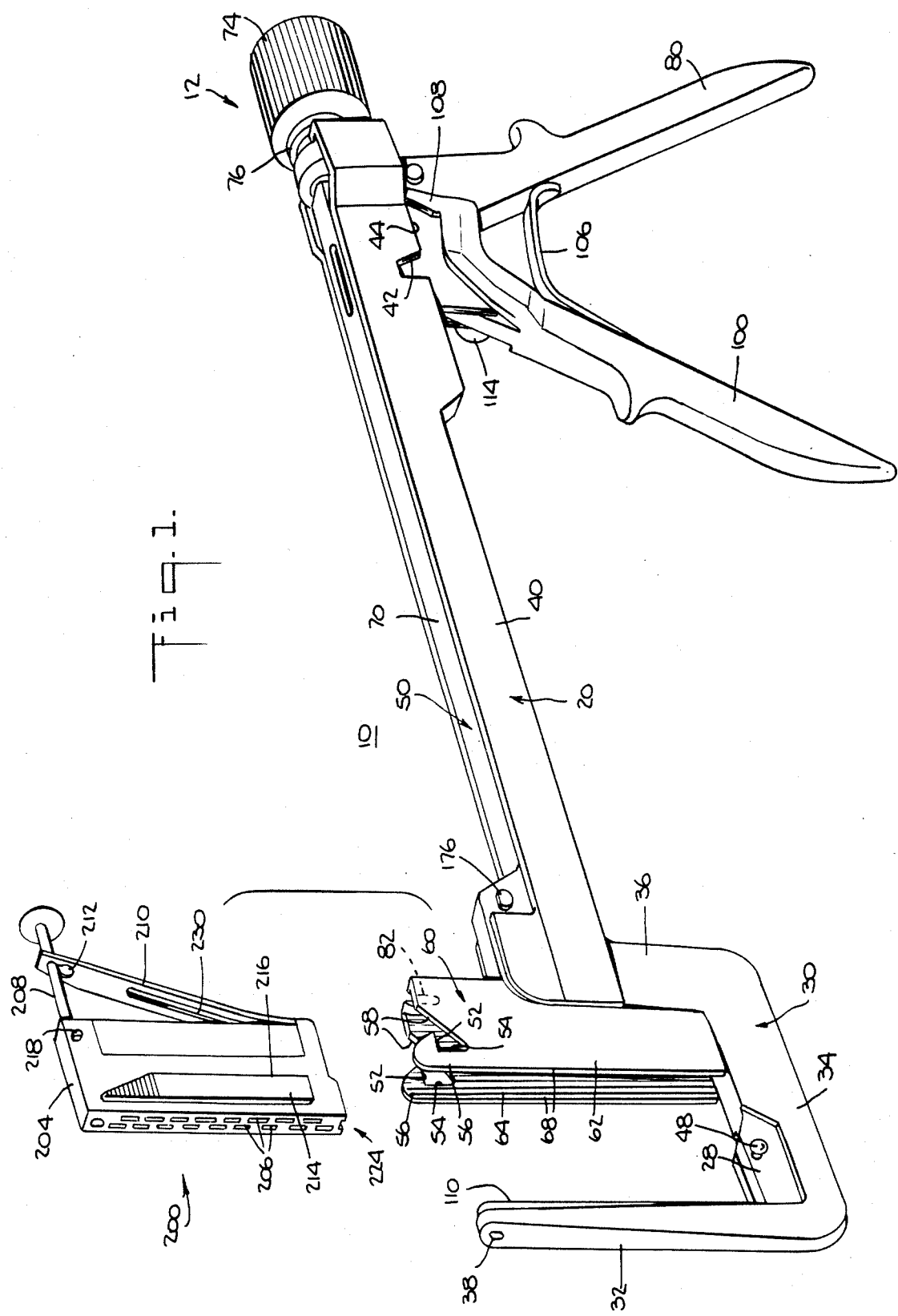
FIG. 1 is a perspective view of a first illustrative embodiment of the invention showing the fastener holding cartridge and the cartridge actuator separate from one another.

As can be seen in FIG. 1, the two principal components of the surgical fastener applying apparatus 10 of this invention are actuator assembly 12 and a surgical fastener containing cartridge 200. Cartridge 200 is removably receivable in actuator 12 as described in detail below. When cartridge 200 is disposed in actuator 12, actuator 12 is operated as described in detail below to drive the surgical fasteners contained in cartridge 200 at least part way through body tissue placed in the instrument in order to fasten the tissue. Cartridge 200 is typically disposable after a single use in order to avoid all difficulty, time, and expense which would otherwise be required to clean, sterilize, and reload the cartridge for reuse. Actuator 12, on the other hand, is typically reusable or "permanent". Of course, cartridge 200 could be made reusable if desired, and actuator 12 could be made disposable if desired.

Actuator 12 includes a frame 20 having a distal U-shaped portion 30 and a proximal longitudinal shaft portion 40. Distal U-shaped frame portion 30 includes a distal leg 32, a base 34, and a proximal leg 36. The longitudinal axes of elements 32, 34, and 36 define a plane (the plane of the paper in FIG. 2) which is sometimes referred to herein as the plane defined by the U. The longitudinal axis of shaft 40 also lies in this plane.

Shaft 40 is a channel-shaped member which opens upwardly as viewed in FIG. 1. Mounted for longitudinal reciprocation in shaft 40 is clamp actuator assembly 50. Clamp actuator assembly 50 includes distal cartridge holder 60, intermediate longitudinal clamp pusher 70, and proximal handle 80. Cartridge holder 60 is a channel-shaped member disposed in the U-shaped portion 30 of frame 20. The channel-shaped member which comprises cartridge holder 60 includes laterally spaced, parallel side members 62 and 64 connected together by proximal base 66 (FIG. 3). Side members 62 and 64 are substantially parallel to the plane defined by the U. The longitudinal axis of the channel defined by cartridge holder 60 is substantially parallel to the distal leg 32 of the U. This channel opens in the distal direction and is also open at both of its ends (i.e., the end adjacent base 34 and the opposite end remote from base 34).

Figure 2:
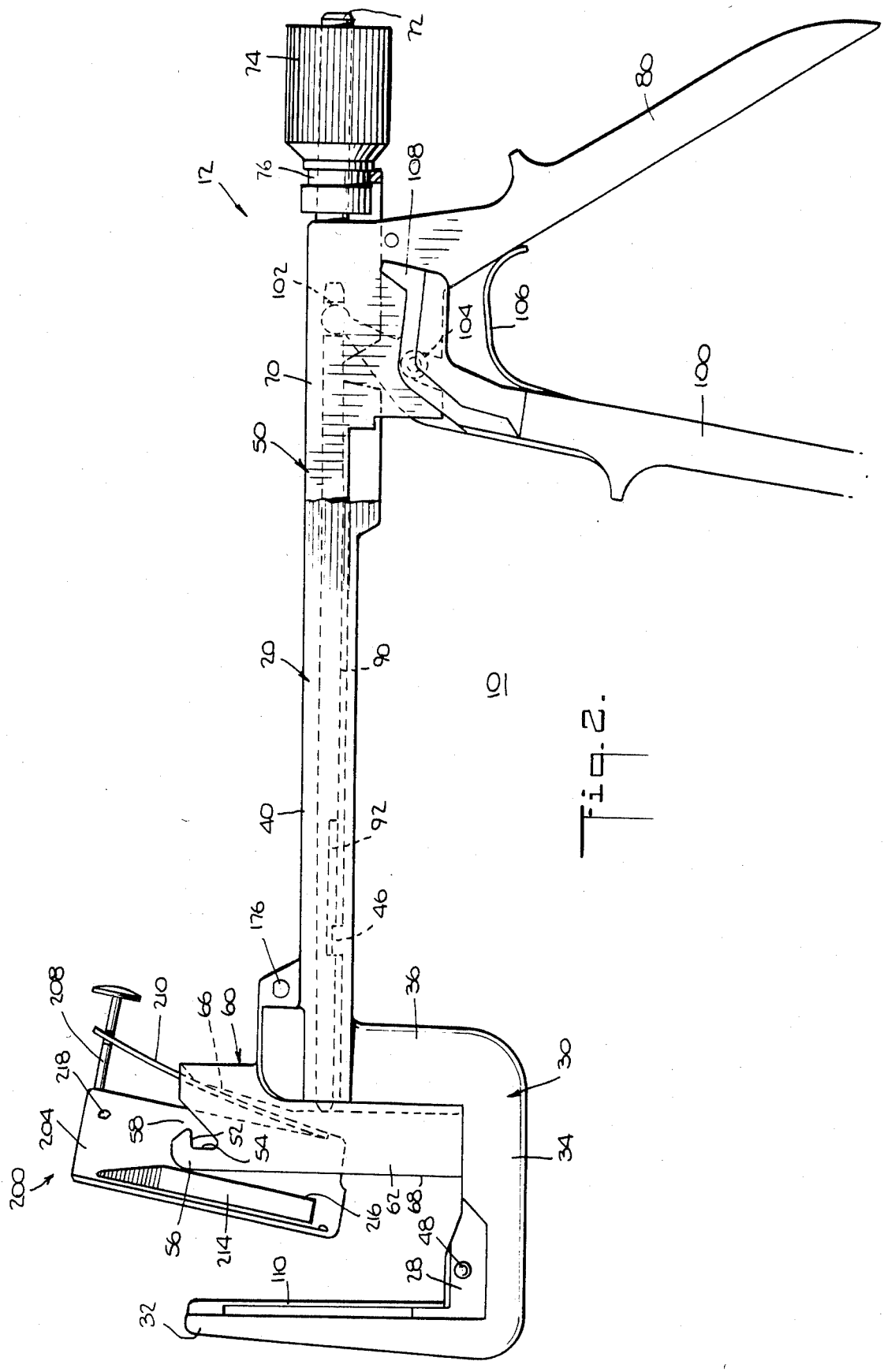
FIG. 2 is a partly sectional elevational view of the apparatus of FIG. 1 showing an early stage in the operation of that apparatus.

Extending from the proximal end of clamp pusher 70 is a threaded stud 72 (FIG. 2). Knurled knob 74 is threadedly mounted on stud 72. The distal shank of knob 74 includes annular recess 76 which is rotatably engaged in a slot in the proximal end of shaft 40. Accordingly, rotation of knob 74 in one direction causes clamp actuator assembly 50 to move distally relative to frame 20, and rotation of knob 74 in the opposite direction causes clamp actuator assembly 50 to move proximally relative to frame 20.

Clamp pusher 70 is also a channel-shaped member which opens downwardly as viewed in FIG. 1. Mounted for longitudinal reciprocation in clamp pusher 70 is fastener pusher 90 (FIGS. 2 and 3). The distal end of fastener pusher 90 communicates with the channel defined by cartridge holder 60. A proximal end portion of fastener pusher 90 receives the upper end portion 102 (FIG. 2) of fastener actuator handle 100. Fastener actuator handle 100 is pivotally connected to clamp pusher assembly 50 by pin 104. Handle 100 is resiliently biased to pivot clockwise about pin 104 as viewed in FIGS. 1 and 2 by leaf spring 106 which is connected to handle 100 at one end and which bears on handle 80 adjacent the other end. When handle 100 is pivoted in the counter-clockwise direction as viewed in FIGS. 1 and 2, fastener pusher 90 moves in the distal direction relative to clamp pusher assembly 50. When handle 100 is released, spring 106 restores handle 100 and fastener pusher 90 to their initial positions relative to clamp pusher assembly 50.

Actuator assembly 12 includes a safety interlock which automatically prevents operation of handle 100 until cartridge holder 60 has been reciprocated toward distal leg 32 by at least a predetermined amount. This safety interlock includes projection 108 on handle 100 and notch 42 in shaft 40. When cartridge holder 60 is retracted proximally from leg 32 as shown in FIGS. 1 and 2, the upper end of projection 108 bears on shaft surface 44 which is proximal of notch 42. This prevents handle 100 from being pivoted counter-clockwise as viewed in FIGS. 1 and 2. As knob 74 is rotated to cause cartridge holder 60 to move distally toward leg 32 handle projection 108 similarly moves distally toward notch 42. When cartridge holder 60 is a predetermined distance from leg 32 as shown in FIG. 7, handle projection 108 can enter notch 42 and handle 100 can be pivoted counter-clockwise as shown in broken lines in FIG. 7. Accordingly, fastener pusher 90 cannot be reciprocated in the distal direction by operation of handle 100 until cartridge holder 60 is less than predetermined maximum distance from leg 32. Because elements 42 and 108 are visible to the operator of the instrument, they also provide a visible proximal indication of whether or not the tissue has been clamped sufficiently for fastening.

In the particular embodiment shown in the drawing, cartridge 200 contains a plurality of U-shaped metal surgical staples 202 (FIG. 8) arranged in two parallel spaced rows. When staples 202 are driven from cartridge 200 as described below, the distal ends of the legs of the staples are clinched or crimped by contact with an anvil member 110 which is mounted on or formed as part of the distal leg 32 of actuator frame 20. Anvil 110 may be a removable and disposable part of the apparatus.

If desired, two-part plastic surgical fasteners of the general type shown in Noiles U.S. Pat. No. 4,060,089 can be used instead of metal staples. In that event, the staple clinching anvil 110 in the embodiment depicted herein would be replaced by a member for supporting the retainer part or parts of the two-part fasteners. The term "surgical fasteners" is used herein as a general term for metal surgical staples, two-part plastic surgical fasteners, and their equivalents. Similarly, the term "anvil" is used herein as a generic term for the anvil used to clinch metal surgical staples, the retainer support member used with two-part plastic surgical fasteners, and the equivalents of these elements.

Cartridge 200 includes a housing 204 having two parallel rows of staple containing apertures 206 on the distal side of the cartridge. Each aperture 206 contains a U-shaped metal staple 202 oriented so that the free ends of the legs of each staple point in the distal direction. An alignment pin 208 is mounted in cartridge 200 for reciprocal motion in a direction parallel to the longitudinal axis of the pin. When cartridge 200 is properly positioned in cartridge holder 60 as described below, pin 208 is located on the side of cartridge 200 remote from base 34 and the longitudinal axis of pin 208 is substantially parallel to base 34. A leaf spring 210 is mounted on the proximal side of cartridge 200 remote from apertures 206. The lower end of spring 210 is attached to cartridge housing 204. The upper end of spring 210 includes an aperture 212. The proximal end of pin 208 passes through aperture 212 and is captured by spring 210 by means of an annular recess in pin 208.

Cartridge housing 204 has several surface features which cooperate with various parts of actuator 12 to insure proper alignment and registration between cartridge 200 and anvil 110 so that when staples 202 are driven from the cartridge, the free ends of the staple legs enter and are clinched by anvil depressions 112. The term "alignment" is generally used herein to refer to the proper positioning of cartridge 200 relative to anvil 110 in the direction perpendicular to the plane defined by the U. The term "registration" is generally used herein to refer to the proper positioning of cartridge 200 relative to anvil 100 in the direction parallel to the longitudinal axis of anvil 110 or distal frame leg 32. The term "parallelism" is generally used herein to refer to positioning of cartridge 200 so that the distal surface of the cartridge is parallel to anvil 110. The term "parallel alignment" is used herein to refer to concurrent "parallelism" and "alignment" (as those terms are defined above) of cartridge 200 relative to anvil 110.

On each of the two lateral sides of cartridge housing 204 is a raised block 214, only one of which is visible in the Figures. The proximal surface 216 of each raised block 214 is a stop surface which is parallel to the distal surface of cartridge 200. Also on each of the two lateral sides of cartridge housing 204 is a laterally extending lug 218. Lugs 218 are proximal of blocks 214 and adjacent the side of cartridge 200 which is remote from base 34 when the cartridge is disposed in actuator 12. The distal facing surfaces of lugs 218 comprise additional stop surfaces 220 (FIG. 3). The surfaces of lugs 218 which face away from base 34 when cartridge 200 is disposed in actuator 12 are cam follower surfaces 222 (FIG. 3). The bottom portion of cartridge housing 204 defines a downwardly facing channel 224. The two laterally spaced inwardly facing side surfaces of channel 224 comprise alignment surfaces 226 (FIG. 12). The bottom surface of channel 224 comprises registration surface 228 (FIG. 3) which is perpendicular to the distal surface of cartridge 200.

Considering now the operation of the apparatus, the instrument is prepared for use by rotating knob 74 to retract cartridge holder 60 from distal frame leg 32 as shown in FIGS. 1 and 2. If anvil 110 is a removable and disposable member, a new anvil is placed on leg 32. Then cartridge 200 is dropped into cartridge holder 60 in the manner depicted in sequential FIGS. 2, 3, and 4. The sides 62 and 64 of cartridge holder 60 are spaced apart by a distance greater than the thickness of cartridge 200 but less than the distance between the free ends of lugs 218 or the free surfaces of raised blocks 214. Accordingly, cartridge 200 drops relatively loosely into the open upper end of cartridge holder 60. Stop surfaces 216 pass along the distal end surfaces 68 of the sides 62, 64 of cartridge holder 60. Lugs 218, on the other hand, enter apertures 58 in the upper ends of side members 62, 64 (see especially FIG. 3). Leaf spring 210 contacts the base 66 of cartridge holder 60. The proximal portion of pin 208 (between spring 210 and the proximal head of the pin) enters slot 82 (FIG. 1) in the base 66 of cartridge holder 60.

It should be noted that during this phase of the insertion of cartridge 200 into cartridge holder 60, the cartridge is inserted along an axis which is distally inclined in the direction of cartridge insertion. The axis of cartridge insertion is therefore transverse to the longitudinal axis of distal frame leg 32. In addition, cartridge 200 is inclined so that it is substantially aligned with the axis of cartridge insertion. Leaf spring 210 must be deflected slightly toward cartridge housing 204 in order to cause lugs 218 to enter apertures 58.

Figure 4:
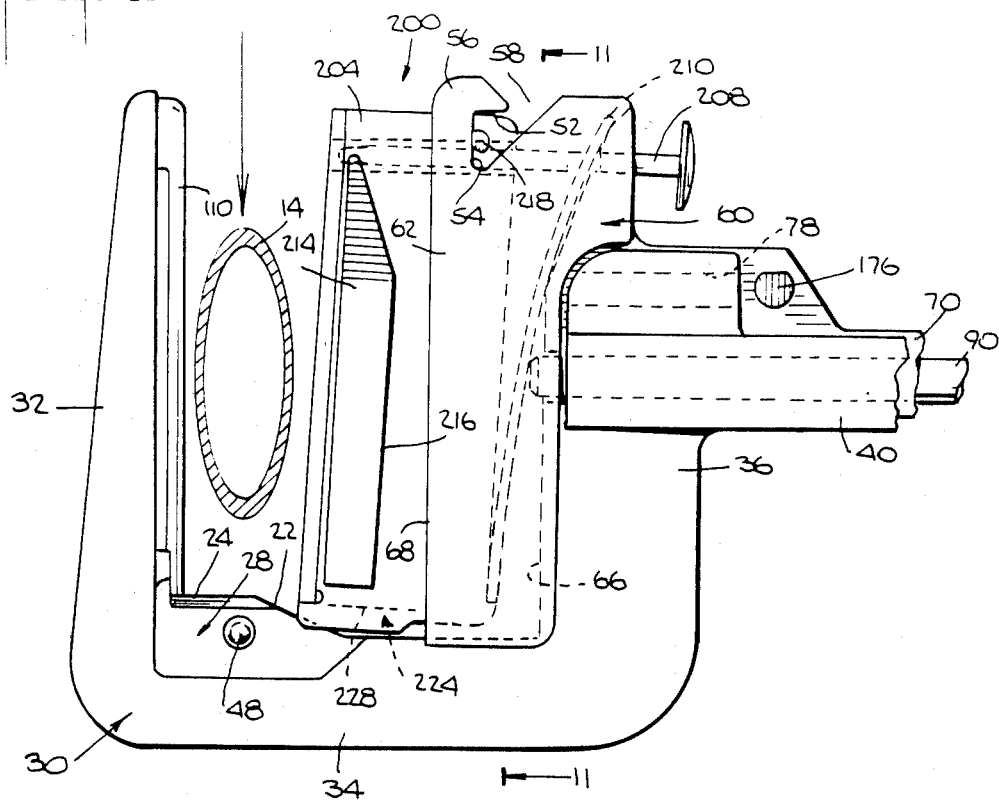

Each of apertures 58 defines the proximal side of a hook-shaped structure 56 which projects upward from the associated side 62, 64 of cartridge holder 60. Each hook structure 56 defines a proximal facing stop surface 54 and a cam surface 52 which faces toward base 34. When lugs 218 begin to enter apertures 58 as shown in FIG. 3, a slight amount of downward manual pressure is applied to cartridge 200 to cause lugs 218 to pass around the proximal ends of hooks 56. When lugs 218 drop below cam surfaces 52, spring 210, which bears on the base 66 of cartridge holder 60, urges cartridge 200 in the distal direction until stop surfaces 220 on lugs 218 contact stop surfaces 54 on hooks 56 as shown in FIG. 4. Thus, once lugs 218 have passed under the proximal ends of hooks 56, spring 210 tends to urge cartridge 200 toward parallelism with anvil 110. Stop surfaces 54 and 220 cooperate to prevent cartridge 200 from moving distally relative to cartridge holder 60 any farther than is shown in FIG. 4. Cam surfaces 52, which are now above lugs 218, cooperate with lugs 218 to prevent cartridge 200 from being removed from cartridge holder 60 along an axis substantially parallel to leg 32. This prevents the cartridge from inadvertently falling out of the actuator.

At the same time that lugs 218 are passing the proximal ends of hooks 56, channel 224 on the bottom of cartridge 200 begins to engage a roll 28 which is formed on base 34. In particular, as shown in FIG. 4, a proximal portion of rail 28 enters a distal portion of channel 224 so that the side surfaces 226 of channel 224 contact the side surfaces 26 of rail 28. In contrast to the relatively loose fit between the sides of cartridges 200 and cartridge holder 60, the fit between the sides 226 of channel 224 and the sides 26 of rail 28 is relatively snug. This begins the process of precisely aligning cartridge 200 with anvil 110. The distal portion 24 of the top surface of rail 28 is perpendicular to anvil 110. The proximal portion 22 of the top surface of rail 28 is inclined downward (away from cam surface 52) in the proximal direction.

The assembled instrument is now ready to receive the tissue 14 to be fastened. Tissue 14 is therefoe positioned between the distal surface of cartridge 200 and anvil 110 as shown in FIG. 4.

Figure 5:
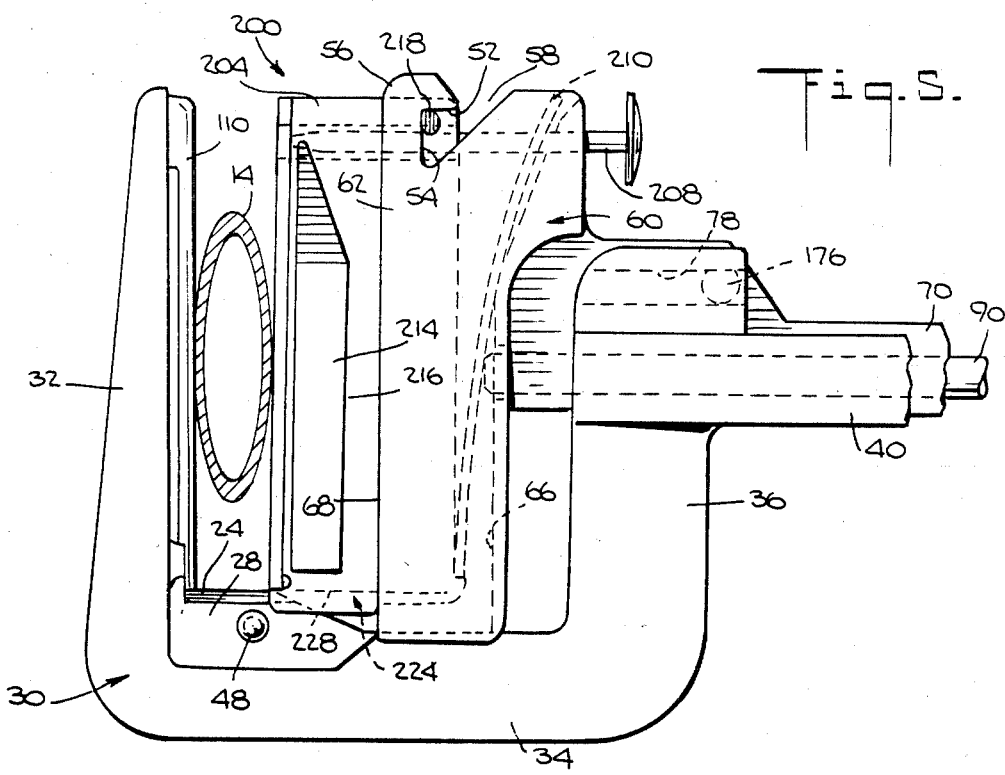
Figure 2:
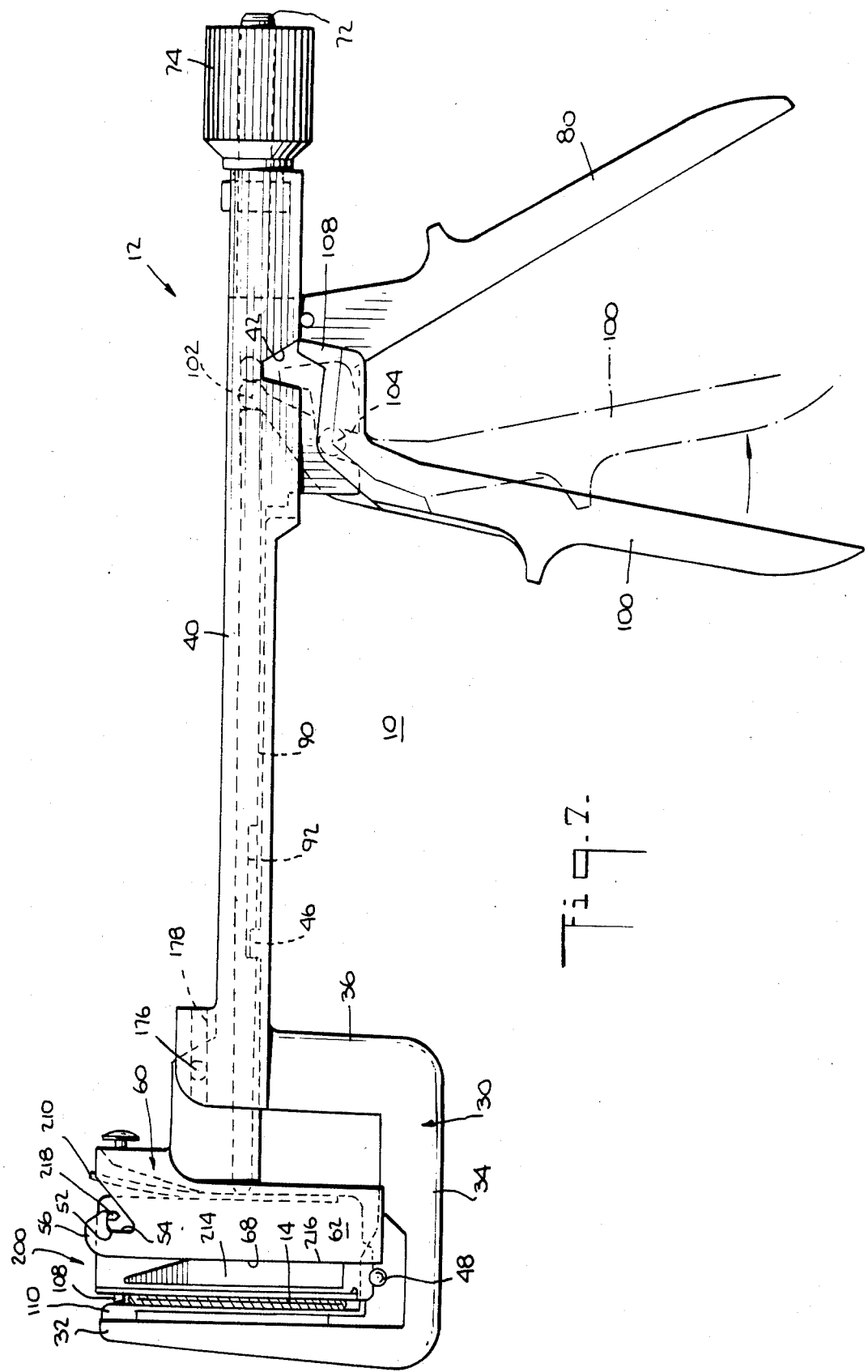

The next step in the operation of the instrument is to clamp tissue 14 between cartridge 200 and anvil 110. This is accomplished by rotating knob 74 to cause cartridge holder 60 to move in the distal direction toward anvil 110 as shown progressively in FIGS. 5-7. As cartridge holder 60 begins to move in the distal direction, spring 210 urges cartridge 200 to move distally with cartridge holder 60. Channel 224 therefore moves distally along rail 28. The bottom surface 228 of channel 224 eventually contacts the inclined top surface portion 22 of rail 28. Thereafter, continued distal motion of cartridge 200 causes the cartridge to shift upwardly in cartridge holder 60 until the bottom surface 228 of channel 224 reaches the portion 24 of the top surface of rail 28 which is perpendicular to anvil 110. This condition of the apparatus is shown in FIG. 5.

At about the time that surfaces 228 and 24 come into contact with one another, the cam follower surface portions 222 of lugs 218 contact cam surfaces 52 on hooks 56. Preferably, the distance between surfaces 24 and 52 is equal to or (most preferably) slightly less than the distance between surfaces 222 and 228, both of these distances being measured parallel to anvil 110. Thus when cam follower surface 222 comes into contact with cam surface 52, these surfaces cooperate to force surface 228 into firm contact with surface 24. This effect of surfaces 52 and 222 is enhanced as cartridge 200 gradually becomes more parallel with anvil 110 as described below. Because cartridge 24 is perpendicular to anvil 110, and because surface 228 is perpendicular to the distal surface of cartridge 200, firm contact between surfaces 24 and 228 provides the necessary registration between the staples 202 in cartridge 200 and the staple clinching depressions 112 in anvil 110.

Continued rotation of knob 74 causes further distal motion of cartridge holder 60 as shown in FIG. 6 until the instrument reaches the condition shown in FIGS. 7 and 8, at which point the tissue is fully clamped and ready to be fastened. During the motion of cartridge holder 60 from the position shown in FIG. 5 to the position shown in FIGS. 7 and 8, cartridge 200 gradually clamps tissue 14 against anvil 110. As pressure is applied to tissue 14, spring 210 compresses against cartridge housing 204 and allows cartridge holder 60 to move distally relative to cartridge 200. This relative distal motion of cartridge holder 60 stops when stop surfaces 68 on the distal ends of cartridge holder sides 62 and 64 contact stop surfaces 216 on cartridge 200 as shown in FIGS. 7 and 8. Because stop surfaces 216 are parallel to the distal surface of cartridge 200, contact between surfaces 68 and 216 assures parallelism between anvil 110 and cartridge 200.

The above-described compression of spring 210 also causes alignment pin 208 to move distally relative to cartridge 200. Accordingly, the distal end of pin 208 automatically extends from cartridge 200 into aperture 38 in anvil 110 and distal frame leg 32 (see FIG. 8). This helps to align the ends of anvil 110 and cartridge 200 which are remote from base 34. Preferably the vertical dimension of aperture 38 (as viewed, for example, in FIG. 8), or the corresponding dimension of the cartridge aperture in which pin 208 reciprocates, or both of these dimensions are substantially greater than the corresponding dimension (i.e., the diameter) of pin 208 so that pin 208 does not contribute to or interfere with proper registration of cartridge 200 as provided by elements 24, 228, 52, and 218. However, in order for pin 208 to contribute to proper alignment of cartridge 200 as described above, the lateral dimension of aperture 38 (i.e., the dimension perpendicular to the plane of the paper in FIG. 8) and the corresponding dimension of the cartridge aperture in which pin 208 reciprocates are preferably equal to the corresponding dimension (i.e., the diameter) of pin 208 plus a small clearance dimension. The aligning action of pin 208 is enhanced by the presence of the proximal portion of pin208 in slot 82 (FIG. 1) in the base 66 of cartridge holder 60. If anvil 110 is removable, the fact that alignment pin 208 must enter aperture 38 in anvil 110 also helps to assure registration of anvil 110 and cartridge 200.

The ends of elements 110 and 200 adjacent base 34 are aligned by contact between surfaces 26 and 226 as described in detail above. Headed pin 48, which, as shown in FIG. 12, extends just beyond the downwardly extending sides of channel 224, helps prevent deformation of these channel legs in the event that torque is applied to cartridge 200 about the longitudinal axis of anvil 110. This may be especially desirable if cartridge housing 204 is made of plastic.

It should be noted that during the above-described distal motion of cartridge holder 60 relative to cartridge 200, lugs 218 move along cam surfaces 52 (compare FIGS. 6 and 8). However, elements 52 and 218 remain in contact with one another, thereby continuing to assure firm contact between registration surfaces 24 and 228 and also preventing removal of cartridge 200 from holder 60.

Figure 9:
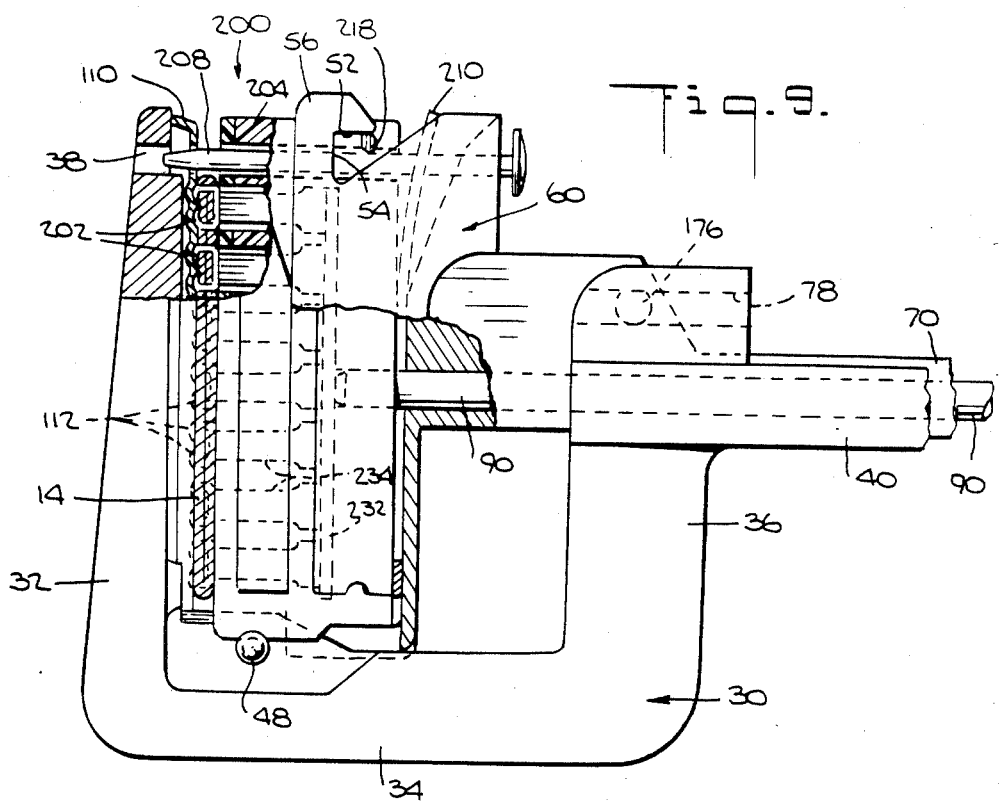
FIGS. 9 and 10 are views generally similar to FIGS. 3-6 and 8 showing successive further stages in the operation of the apparatus of FIG. 1.

As mentioned above, when tissue 14 is fully clamped, handle projection 108 is adjacent notch 42 as shown in FIG. 7. This makes it possible to pivot handle 100 counter-clockwise as shown in broken lines in FIG. 7. When handle 100 is pivoted counter-clockwise, fastener pusher 90 moves in the distal direction relative to clamp actuator assembly 50, as shown in FIG. 9. The distal end of fastener pusher 90 passes through slot 230 (FIG. 1) in spring 210 and enters the proximal side of cartridge 200. There it contacts a transverse member 232 and drives that member in the distal direction. (If desired, the end of pusher 90 may be made T-shaped to help assure that transverse member 232 remains perpendicular to pusher 90 as member 232 moves distally.) Transverse member 232 in turn drives individual staple pushers 234 in the distal direction. Each individual staple pusher 234 is associated with a respective one of staples 202 so that pushers 234 drive all of staples 202 from cartridge 200. The legs of staples 202 pass through tissue 14, enter anvil depressions 112, and are thereby clinched or crimped to fasten the tissue as shown in FIG. 9. The travel of fastener pusher 90 is preferably limited by cooperation of lug 46 (FIG. 2) on frame 20 projecting into recess 92 in fastener pusher 90. This prevents overcompression of staples 202.

Figure 10:
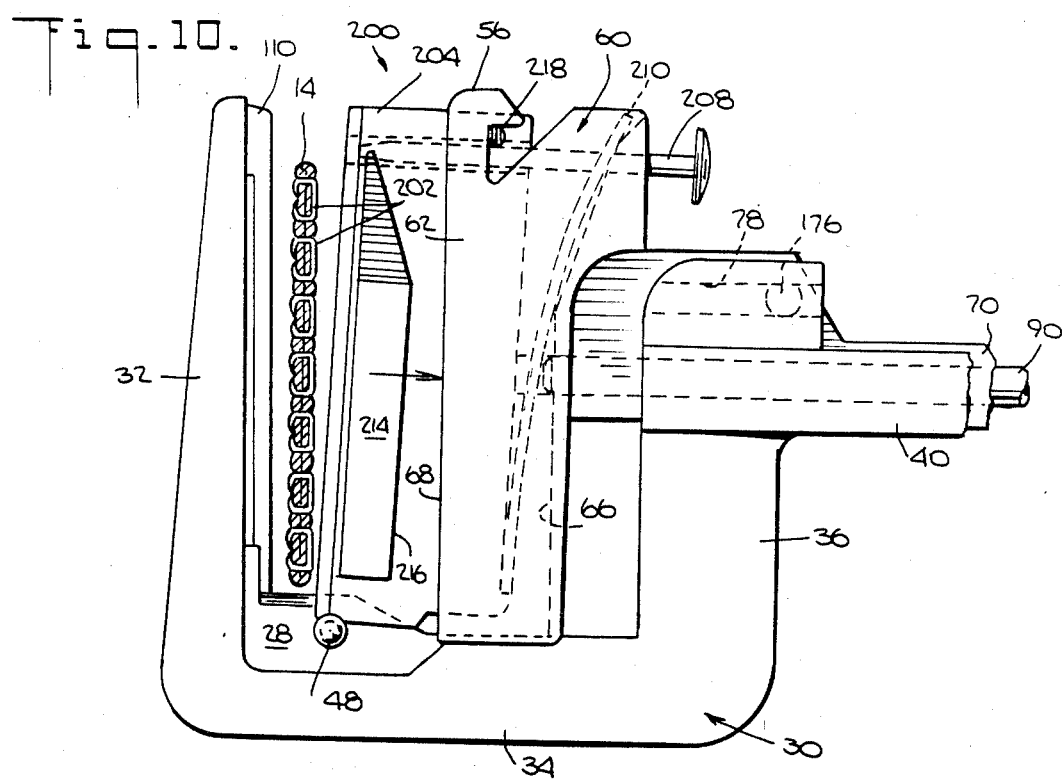

After staples 202 have been driven, handle 100 is released. Spring 106 restores handle 100 and fastener pusher 90 to their initial positions. The fastened tissue can be removed from the instrument by rotating knob 74 to retract cartridge holder 60 in the proximal direction as shown in FIG. 10. This also retracts cartridge 200, thereby relieving the clamping pressure on the tissue, and allowing spring 210 to flex away from cartridge housing 204. This in turn allows spring 210 to retract pin 208. The fastened tissue can then be removed from the instrument. In addition, cartridge 200 can be removed from actuator 12 by a manipulation which is the reverse of cartridge insertion.

Cartridge insertion and removal are quick and easy because cartridge 200 fits relatively loosely into carriage holder 60. Precise alignment and registration of cartridge 200 and anvil 110 are achieved automatically after the cartridge has been inserted in actuator 12 (i.e., during operation of the actuator to clamp the tissue). In addition, substantially all of the elements which align and register cartridge 200 and anvil 110 are confined to the cartridge itself and elements of the actuator which are immediately adjacent to anvil 110 (i.e., rail 28 and aperture 38). This makes it possible to manufacture the remaining major portion of actuator 12 with less stringent tolerances, thereby reducing the initial cost of the actuator and making it easier and less expensive to maintain.

Another advantage of the disclosed apparatus is that alignment pin 208 is an integral part of cartridge 200. The operator of the instrument does not have to separately handle pin 208. Moreover, pin 208 operates automatically when the tissue is clamped in the instrument to perform its function of helping to align cartridge 200 and anvil 110.

Actuator 12 can be easily disassembled to facilitate cleaning. Pivot pin 104 can be disengaged by rotating knob 114 (FIG. 1). When pin 104 is disengaged, handle 100 can be removed from clamp actuator assembly 50. When clamp actuator assembly 50 is retracted sufficiently far in the proximal direction relative to frame 20, lugs 176 on clamp pusher 70 come out of longitudinal slots 78 (FIG. 3) in frame 20 as shown in FIG. 1. With handle 100 removed, frame 20 can be moved down relative to clamp actuator assembly 50 and completely separated from that assembly. Fastener pusher 90 will slide distally out of assembly 50 once frame 20 is removed. Knob 74 can also be removed from assembly 50. Actuator 12 is reassembled by reversing the foregoing procedure.

II. Second Illustrative Embodiment

A second illustrative embodiment of the invention is shown in FIGS. 14–23. Elements in this embodiment which are the same as or similar to elements in the first embodiment are identified by reference numbers which are 300 more than the reference numbers used in FIGS. 1–13. For example, anvil member 410 in this embodiment may be substantially identical to anvil member 110 in the first embodiment, but longitudinal slot 432 in this embodiment has no counterpart element in the first embodiment and the reference number 132 is accordingly not used anywhere in this application. The proximal portion of actuator assembly 312 in this embodiment may be similar to the corresponding portion of actuator assembly 12 in the first embodiment and is therefore not repeated in FIGS. 14–23.

Cartridge holder 360 is similar to cartridge holder 60 in the first embodiment, with the following exceptions: The upper portions of distal end surfaces 368 are inclined somewhat in the proximal direction as indicated at 368a. A preliminary cartridge registration slot 460 is provided in each of side members 362 and 364.

Figure 17:
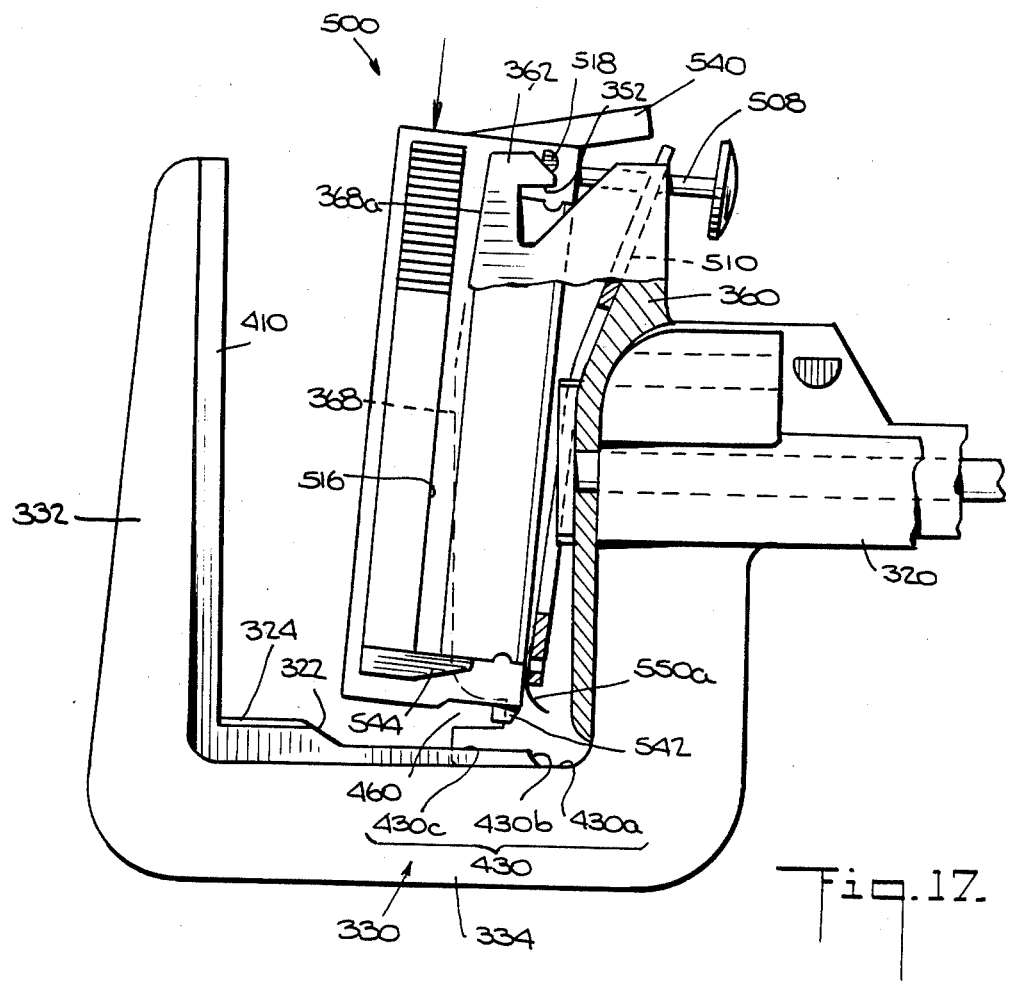
FIG. 17 is a partly sectional elevational view of a part of the apparatus of FIG. 14 showing an early stage in the operation of that apparatus.
Figure 15:
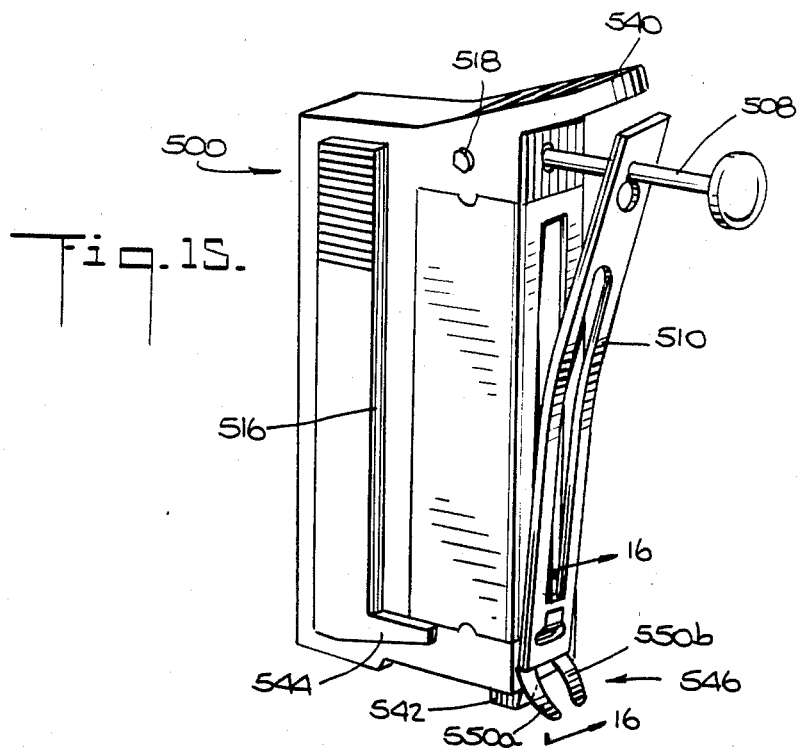
FIG. 15 is a perspective view of the fastener holding cartridge of FIG. 14.

The distal U-shaped portion 330 of frame 320 is similar to distal U-shaped portion 30 of frame 20 in the first embodiment, with the following exceptions: In addition to top surface portions 322 and 324 which are respectively similar to portions 22 and 24 in the first embodiment, the upper surface of base 334 includes a cam surface portion 430 having segments 430a, 430b, and 430c (FIG. 17). A longitudinal slot 432 (FIG. 14) is provided in segments 430b and 430c. Slot 432 extends into top surface portion 322. Headed pin 48 is not present in the second embodiment.

Cartridge 500 is similar to cartridge 200 in the first embodiment, with the following exceptions: Stop surfaces 516 do not have the distally inclined upper portions found on stop surfaces 216 in the first embodiment. Spring 510 is slightly distally convex. The upper portion of cartridge 500 includes proximally extending tab 540. The bottom surface of cartridge 500 includes downwardly projecting tab 542 adjacent the proximal side of the cartridge. On each side of cartridge 500 a lug 544 extends laterally outward. Lugs 544 are located proximally of stop surfaces 516 adjacent the lower portion of those surfaces. Spring 510 is mounted on another mounting spring 546 (FIG. 16). Mounting spring 546 has one portion 548 which extends distally into the body of cartridge 500 for attachment thereto. Mounting spring 546 has two other laterally spaced portions 550a and 550b (FIG. 15) which extend downwardly and in the proximal direction adjacent tab 542.

The operation of the second embodiment is generally similar to the operation of the first embodiment, with the following exceptions: Cartridge 500 is placed in cartridge holder 360 in generally the same manner as in the first embodiment. If cartridge 500 is inadvertently not pushed far enough down in order for lugs 518 to drop below cam surface 352 (i.e., if cartridge 500 is only inserted to the position shown in FIG. 17), lugs 544 enter preliminary cartridge registration slots 460 when cartridge holder 360 begins to move toward distal leg 332. The inclined upper sides of slots 460 contact the proximal ends of lugs 544 and cam cartridge 500 downwardly, thereby pulling lugs 518 below cam surfaces 352. Accordingly, slots 460 and lugs 544 cooperate to provide means for preliminarily registering cartridge 500 with anvil member 410.

Figure 18:
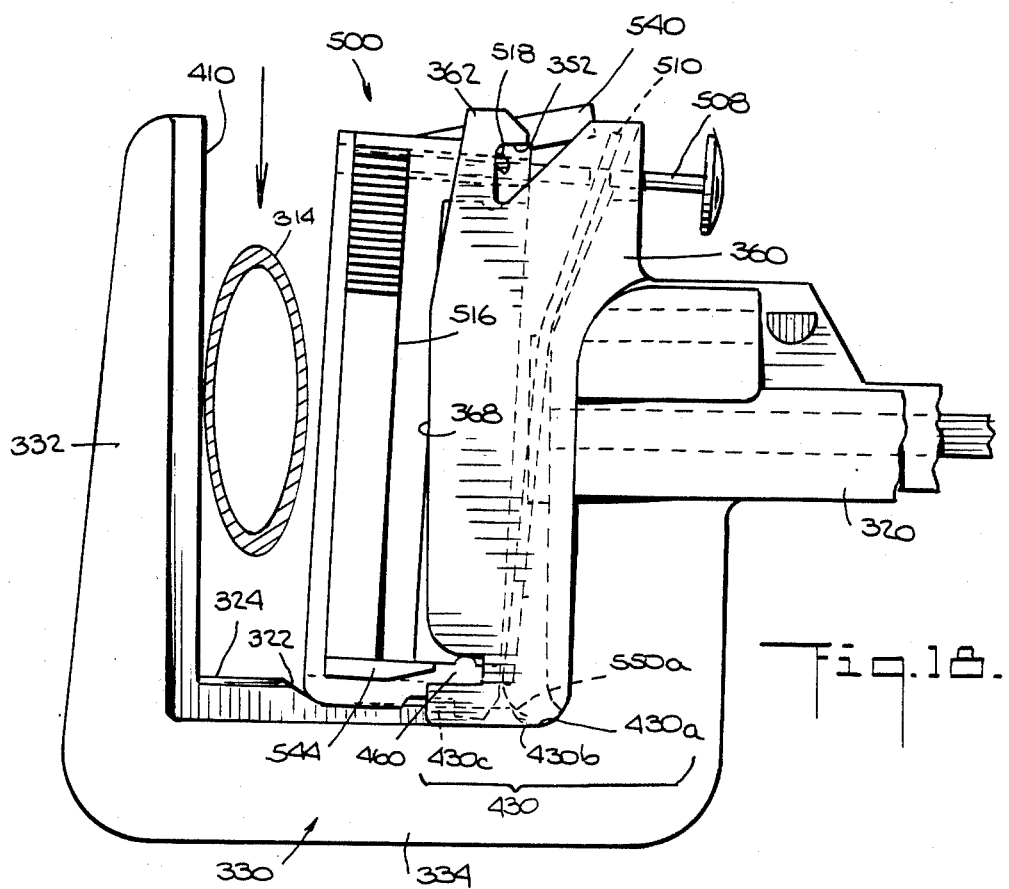
FIGS. 18-23 are views generally similar to FIG. 17 showing successive further stages in the operation of the apparatus of FIG. 14.
Figure 19:
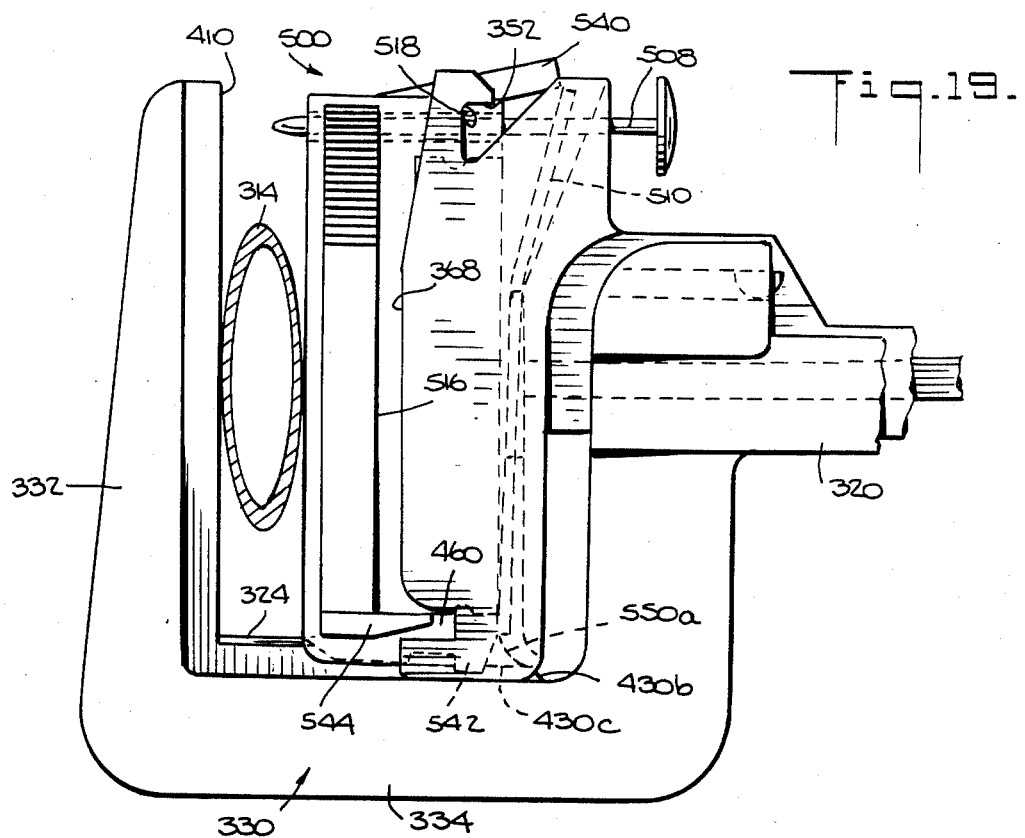
Figure 20:
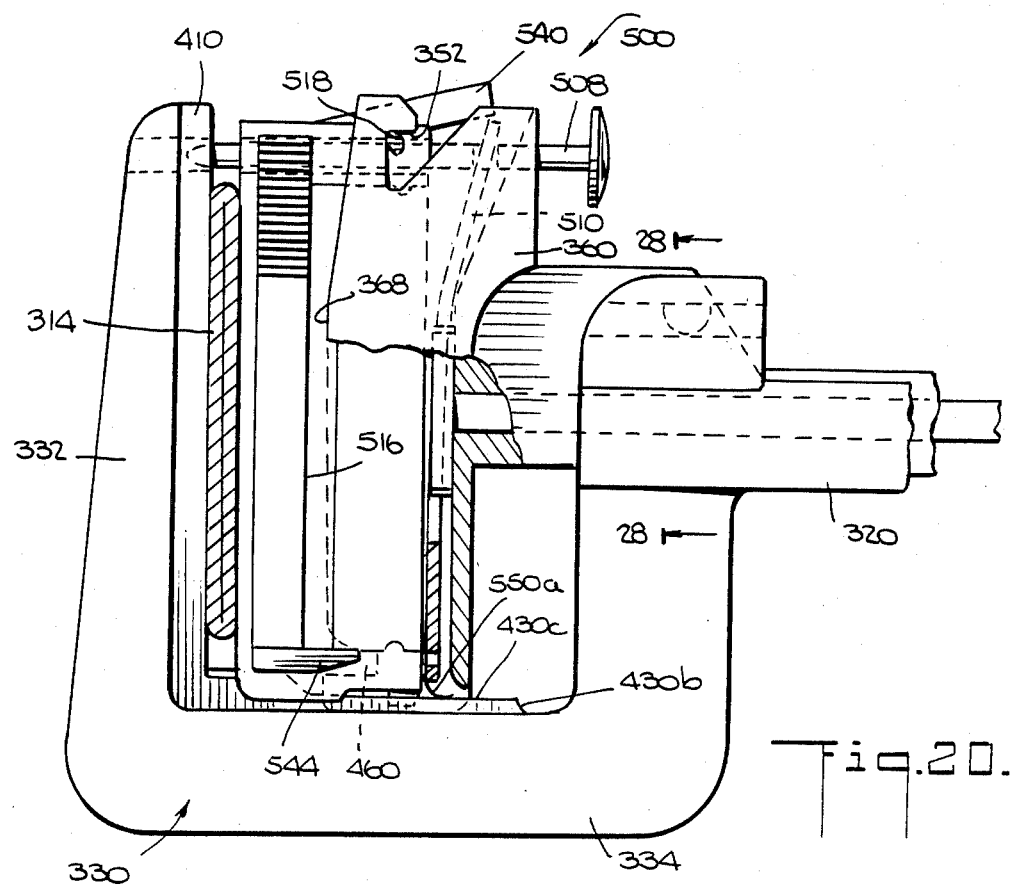
Figure 21:
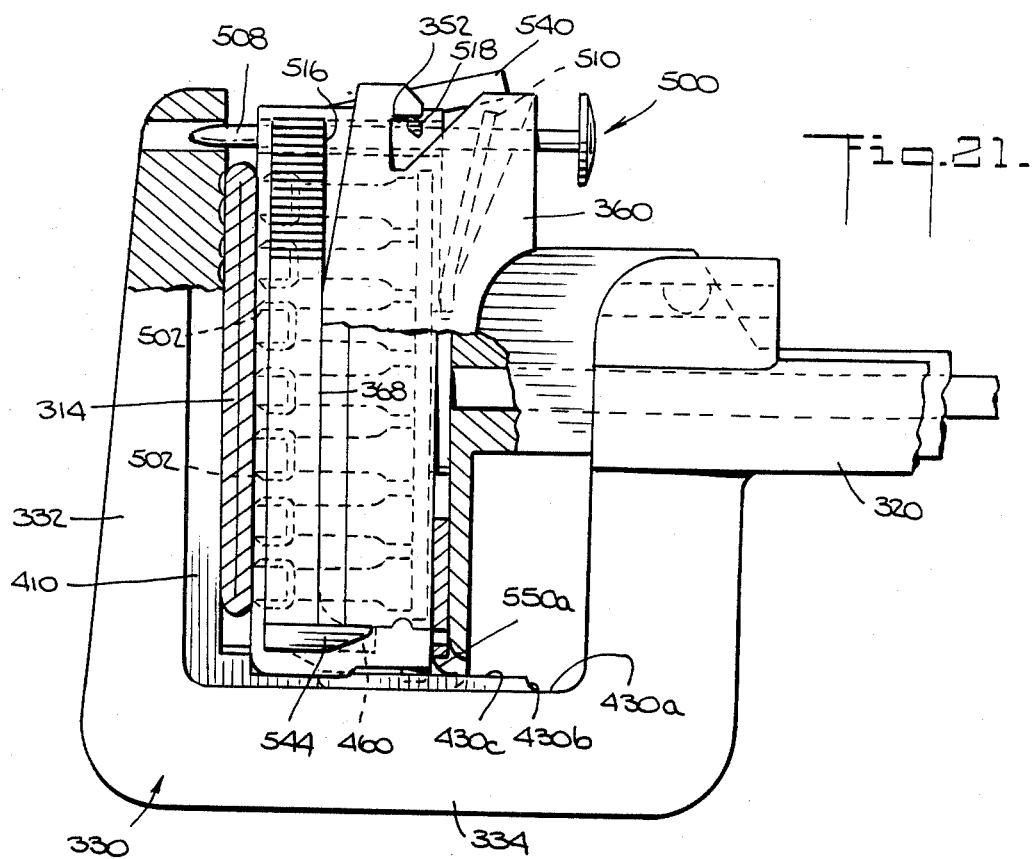
Figure 22:
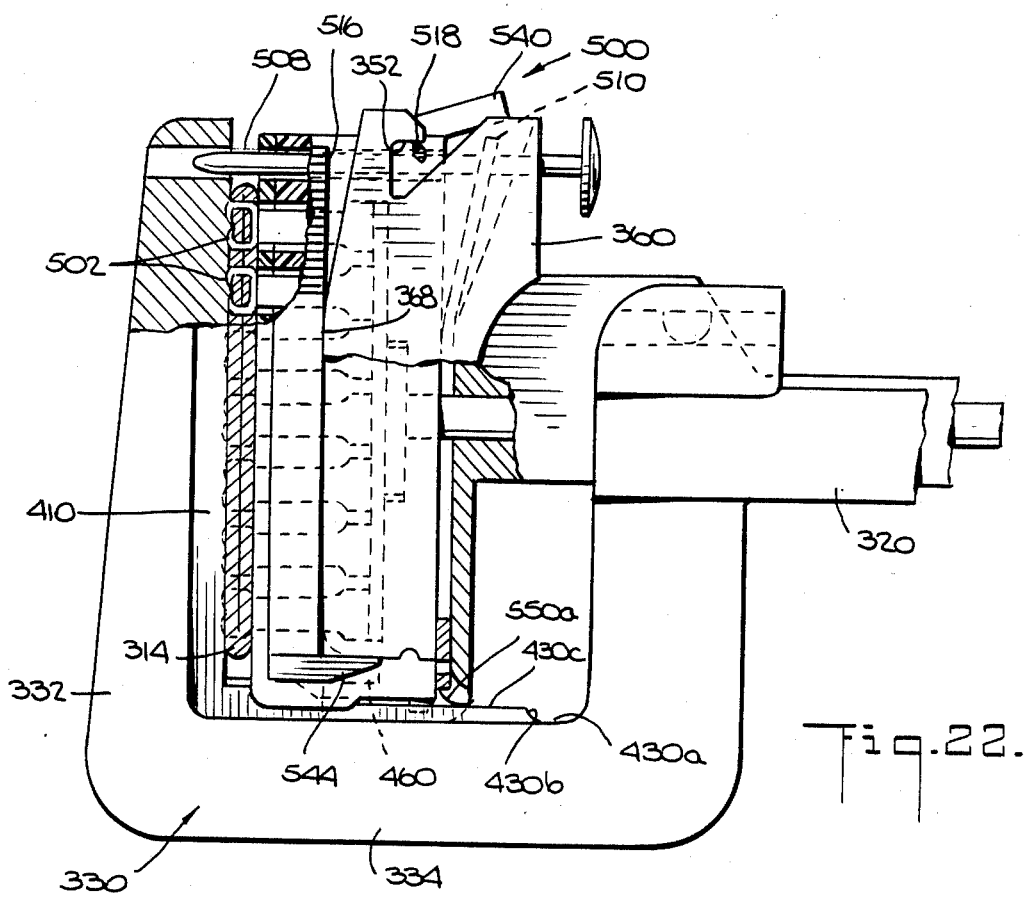

Assuming that cartridge 500 is inserted fully into cartridge holder 360 before the cartridge holder is advanced toward distal leg 332 (i.e., assuming that cartridge 500 is inserted to the position shown in FIG. 18), the lower ends of downwardly extending mounting spring portions 550a and 550b are initially disposed on the proximal side of inclined cam surface segment 430b as shown in FIG. 18. Accordingly, when cartridge holder 360 is subsequently advanced toward distal leg 332 as shown in FIG. 19, spring portions 550a and 550b immediately or almost immediately contact inclined cam surface segment 430b. This pivots spring portions 550a and 550b counter-clockwise as viewed in FIG. 19 so that spring 510 also pivots counter-clockwise. This in turn causes the distal end of alignment pin 508 to extend distally toward distal leg 332 substantially earlier than in the first embodiment. This may be desirable in order to close or partly close as soon as possible the normally open side of the U-shaped space into which the tissue 314 has been inserted. This helps prevent the tissue from escaping or extruding from the instrument as the tissue clamping mechanism is operated.

Lug 542 enters slot 432 in order to help guide cartridge 500 as it reciprocates toward distal leg 332.

Figure 23:
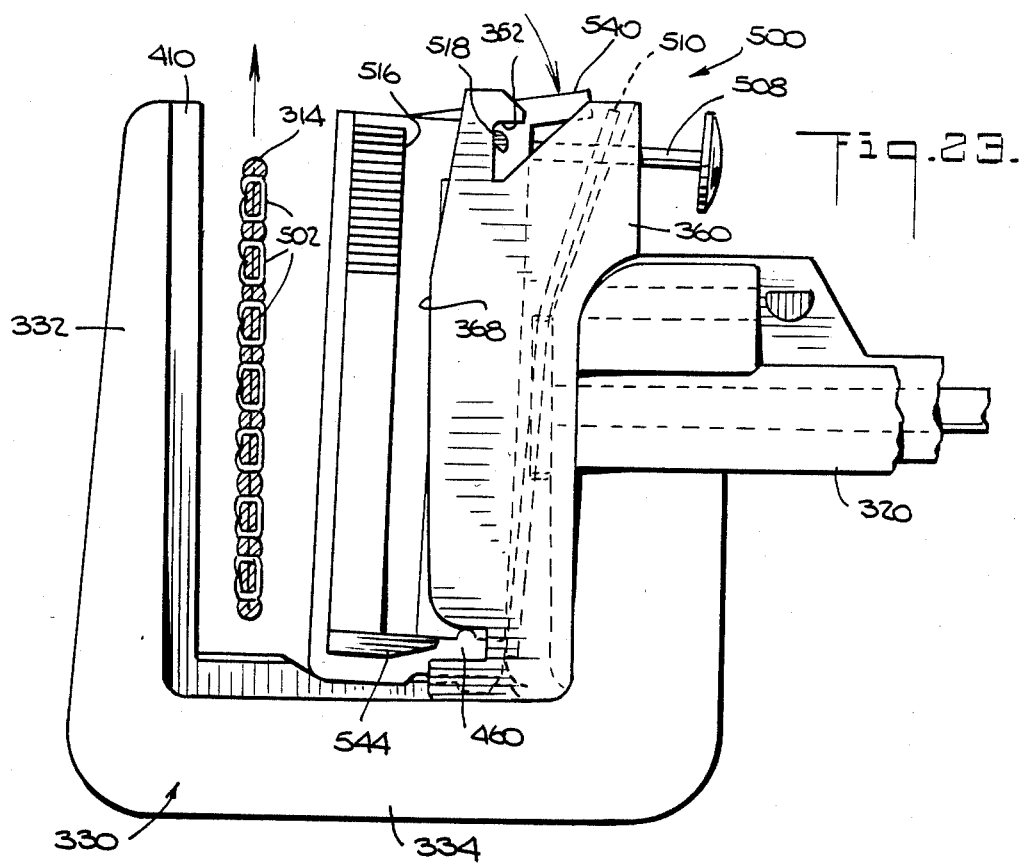
Figure 24:
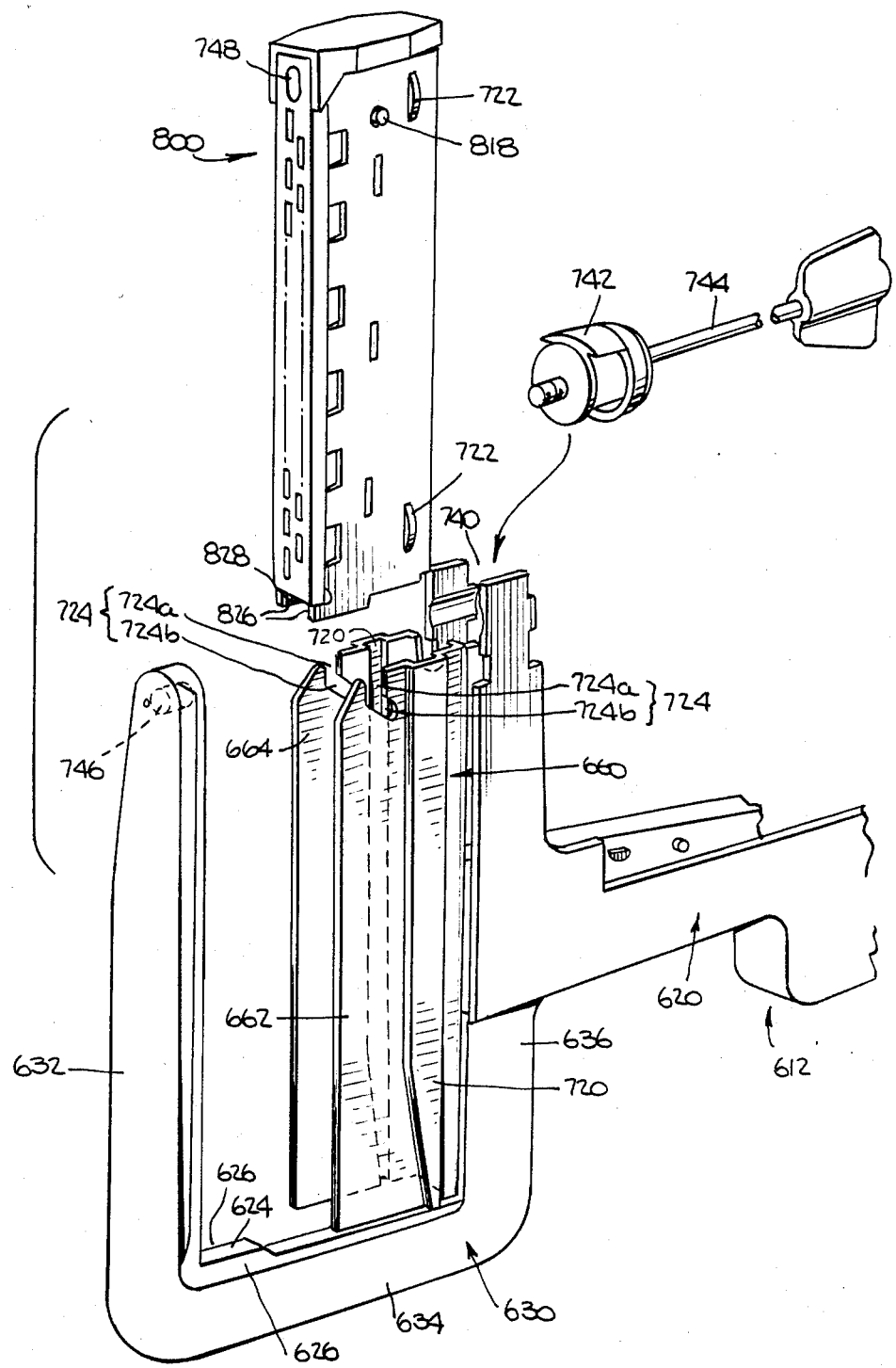
FIG. 24 is a partial perspective view of a third illustrative embodiment of the invention showing the fastener holding cartridge and the cartridge actuator separate from one another.

After staples 502 have been applied to tissue 314 and cartridge holder 360 has been retracted as shown in FIG. 23, downward manual pressure on lug 540 helps to rotate cartridge 500 clockwise as viewed in FIG. 23. This removes lugs 544 from slots 460 and facilitates subsequent removal of cartridge 500 from cartridge holder 360.

III. Third Illustrative Embodiment

A third illustrative embodiment of the invention is shown in FIGS. 24–30. Elements in this embodiment which are the same as or similar to elements in the first embodiment are identified by reference numbers which are 600 more than the reference numbers used in FIGS. 1–13. The proximal portion of actuator assembly 612 in this embodiment may be similar to the corresponding portion of actuator assembly 12 in the first embodiment and is therefore not repeated in FIGS. 24–30.

Cartridge holder 660 is similar to cartridge holder 60 in the first embodiment, with the following exceptions: Each of side members 662 and 664 has a groove 720 which extends vertically as viewed in FIG. 24 from the top of cartridge holder 660 to the bottom of the cartridge holder and which opens into the interior of the cartridge holder. Grooves 720 receive ears 722 which extend laterally outward from the sides of cartridge 800. Each of side members 662 and 664 has a slot 724, each of which includes a vertical initial portion 724a and a final portion 724b which is inclined downwardly and in the proximal direction from the bottom of the initial portion. Although shaped differently than apertures 52 in the first embodiment, slots 724 perform a similar function. In particular, slots 724 receive lugs 818 on cartridge 800.

The distal U-shaped portion 630 of frame 620 is similar to distal U-shaped portion 30 of frame 20 in the first embodiment with the following exceptions: The upper portion of proximal leg 636 defines a cleft 740 into which collar 742 on alignment pin 744 fits as shown, for example, in FIG. 25. There is a releasable detent engagement between collar 742 and the sides of cleft 740. Aperture 746 in distal leg 632 is threaded to receive and threadedly engage the threaded distal end of alignment pin 744. Headed pin 48 is not present in the third embodiment.

Cartridge 800 is similar to cartridge 200 in the first embodiment, with the following exceptions: Four ears 722 (two on each side of the cartridge) extend laterally from the sides of cartridge 800. Ears 722 perform a function similar to stop surfaces 216 in the first embodiment. Cartridge 800 does not have an integral alignment pin structure. Rather, alignment pin 744 and collar 742 are a separate structure.

The operation of the third embodiment is generally similar to the operation of the first embodiment, with the following exceptions: Collar 742 is placed in cleft 740 with alignment pin 744 retracted proximally as shown in FIG. 25. Cartridge 800 is then dropped into cartridge holder 660 so that ears 722 project into grooves 720 and lugs 818 (only one of the two of which is visible in FIGS. 24–30) project into slots 724. This step is shown in FIGS. 25 and 26. Grooves 720 are substantially wider than the thickness of ears 722 so that cartridge 800 drops loosely and easily into cartridge holder 660. The tissue 614 to be stapled is then inserted between the distal surface of cartridge 800 and distal leg 632 as shown in FIG. 26.

When tissue 614 is properly positioned, alignment pin 744 is pushed distally through collar 742, through aperture 748 in cartridge 800, and into aperture 746 in distal leg 632 as shown in FIG. 27. Alignment pin 744 is turned in order to threadedly engage the distal end of pin 744 in aperture 746. The tissue is now ready to be clamped and stapled.

Actuator 612 is operated as in the first embodiment to cause cartridge holder 660 to move in the distal direction as shown in FIG. 28. As cartridge holder 660 moves distally, cartridge 800 begins to clamp tissue 614 against distal frame leg 632. The resistance of tissue 614 to the resulting clamping pressure forces ears 722 against the proximal sides of grooves 720. This forces cartridge 800 into parallelism with the longitudinal axis of frame leg 632. At the same time, the inclined final portions 724b of slots 724 act as cam surfaces in relation to lugs 818, thereby forcing registration surface 828 on the bottom of cartridge 800 downwardly into firm contact with the distal portion 624 of the top surface of the base 634 of distal U-shaped portion 630. This assures proper registration of cartridge 800 with the anvil structure 710 on distal leg 632. Proper alignment of cartridge 800 with anvil structure 710 is further assured by firm contact between alignment surfaces 826 on cartridge 800 and side surfaces 626 on base 634, and by alignment pin 744 in cooperation with aperture 746.

Figure 30:
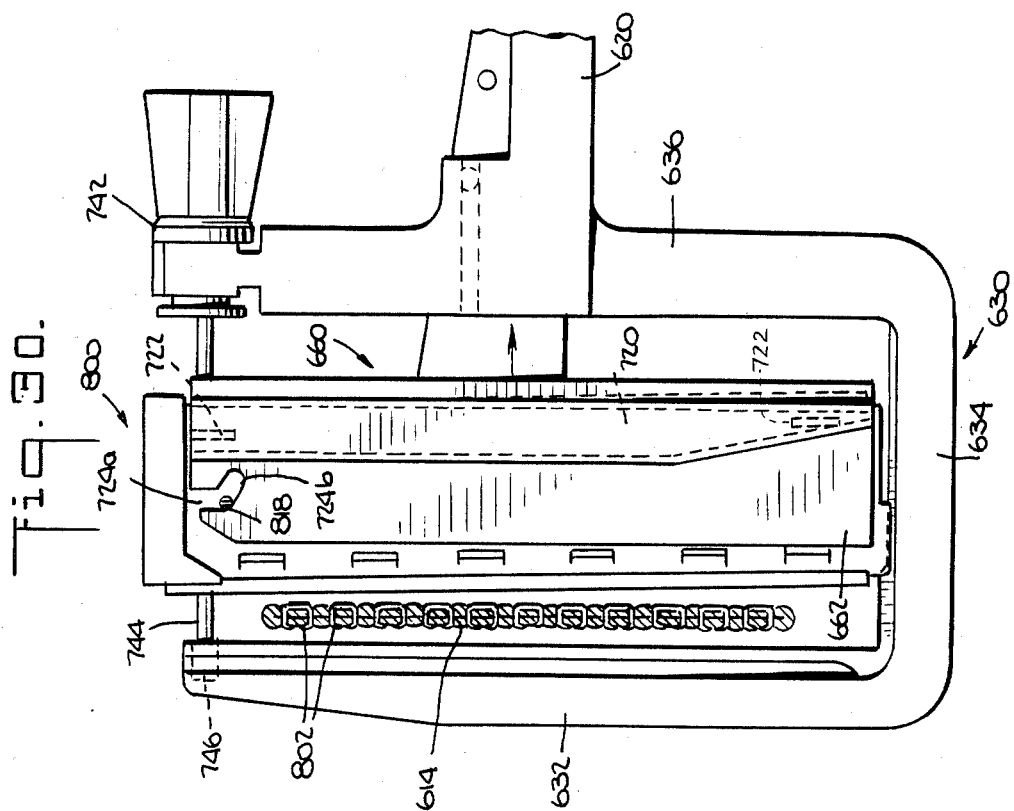
Figure 29:
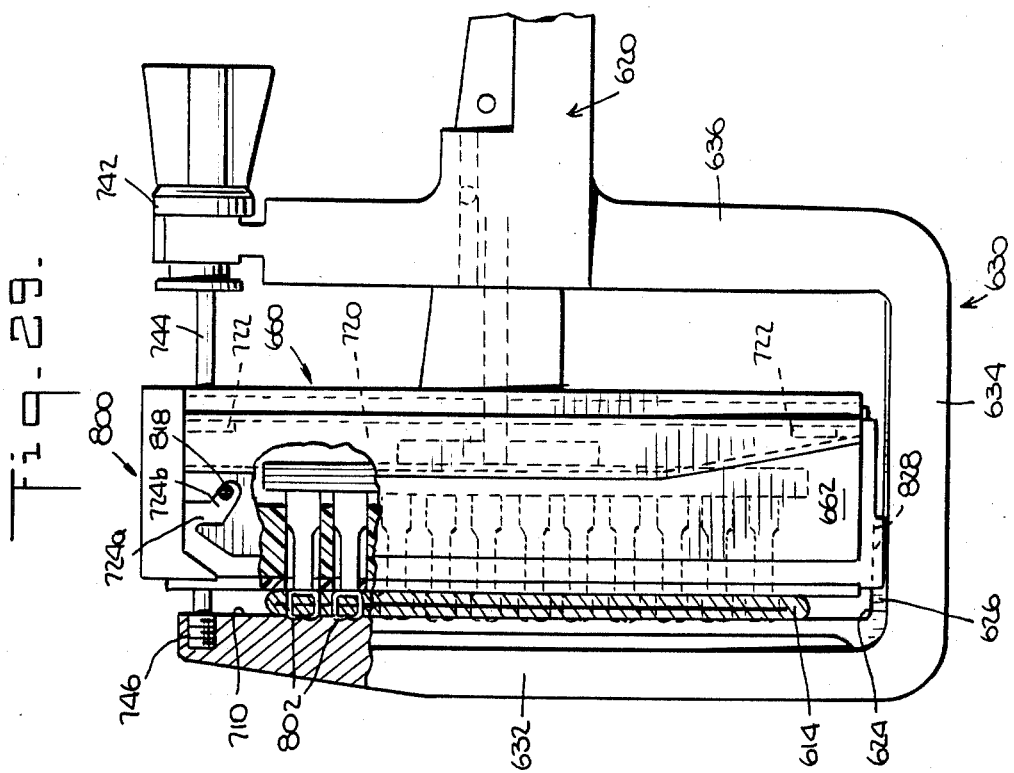

When tissue 614 is fully clamped in the apparatus as shown in FIG. 28, actuator 612 can be operated as in the first embodiment to drive staples 802 through the tissue and against anvil structure 710 as shown in FIG. 29. After the tissue has been stapled, cartridge holder 660 is retracted to release the clamping pressure on the tissue as shown in FIG. 30. Alignment pin 744 can then be unscrewed from aperture 746, retracted from cartridge 800, and removed from actuator 612. Once alignment pin 744 is retracted, the stapled tissue and cartridge 800 can be removed from the instrument.

It will be understood that the foregoing is merely illustrative of the principles of the invention, and that various modifications can be made by those skilled in the art without departing from the scope and spirit of the invention. For example, two-part plastic surgical fasteners can be substituted for metal staples 202 or 502 as discussed in detail above.

I claim:

1. For use in a surgical fastener applying instrument having (a) a frame with a U-shaped distal portion including a distal leg, a proximal leg, and a base interconnecting the distal and proximal legs, (b) anvil means mounted on the distal leg of the U, and (c) cartridge holder means disposed in the U for linear reciprocal motion toward and away from the anvil means, a cartridge comprising:

means for cooperating with the cartridge holder means to removably admit the cartridge into the cartridge holder means by relative motion of the cartridge along an axis transverse to the axis of reciprocation of the cartridge holder means and in a direction along said transverse axis toward the base of the U when the cartridge holder means is linearly reciprocated away from the anvil means; and first cartridge registration means for cooperating with the cartridge holder means to cause the cartridge to move transverse to the axis of reciprocation of the cartridge holder means to bring the cartridge into registration with the anvil means in response to reciprocation of the cartridge holder means toward the anvil means.

2. The cartridge defined in claim 1 further comprising:
an alignment pin mounted adjacent the end of the cartridge remote from the base of the U for linear reciprocal motion substantially parallel to the axis of reciprocation of the cartridge holder means; and
alignment pin advancing means for cooperating with the surgical fastener applying instrument and causing the alignment pin to reciprocate toward the anvil means in response to reciprocation of the cartridge holder means toward the anvil means.

3. The cartridge defined in claim 2 wherein the surgical fastener applying instrument has a cam surface on the base of the U and wherein the alignment pin advancing means comprises:
cam follower means disposed on the cartridge for cooperating with the cam surface on the base of the U and causing the alignment pin to move toward the anvil means substantially faster than the cartridge moves toward the anvil means as the cartridge holder means reciprocates toward the anvil means.

4. Surgical fastener applying apparatus comprising:
a frame having a U-shaped distal portion, the U having a distal leg, a proximal leg, and a base interconnecting the distal and proximal legs;
anvil means disposed on the distal leg of the U;
cartridge holder means disposed in the U for linear reciprocal motion toward and away from the anvil means;
cartridge means;
first means associated with the cartridge holder means and the cartridge means for allowing the cartridge means to be removably inserted in the cartridge holder means along an axis transverse to the axis of reciprocation of the cartridge holder means and in a direction along said transverse axis toward the base of the U in response to linear reciprocation of the cartridge holder means away from the anvil means; and
cartridge registration means associated with the cartridge holder means and the cartridge means for causing the cartridge means to move transverse to the axis of reciprocation of the cartridge holder means to bring the cartridge means into registration with the anvil means in response to linear reciprocation of the cartridge holder means toward the anvil means.

5. The apparatus defined in claim 4 wherein the cartridge registration means comprises:
cam surface means associated with one of the cartridge holder means and the cartridge means and including a portion which is transverse to both the distal leg and the base of the U; and
cam follower means associated with the other of the cartridge holder means and the cartridge means for contacting and traversing the cam surface means when the cartridge holder means is reciprocated toward the anvil means.

6. The apparatus defined in claim 4 wherein the cartridge means includes:
an alignment pin mounted adjacent the end of the cartridge means remote from the base of the U for linear reciprocal motion substantially parallel to the axis of reciprocation of the cartridge holder means; and
alignment pin advancing means for causing the alignment pin to reciprocate toward the anvil means in response to reciprocation of the cartridge holder means toward the anvil means.

7. The apparatus defined in claim 6 wherein the alignment pin advancing means comprises:
cam surface means disposed on the base of the U; and
cam follower means disposed on the cartridge means and operatively connected to the alignment pin advancing means for traversing the cam surface means as the cartridge holder means is reciprocated toward the anvil means and for causing the alignment pin to move toward the anvil means substantially faster than the cartridge means moves toward the anvil means in response to said traversing of the cam surface means.

8. For use in a surgical fastener applying instrument having (a) a frame with a U-shaped distal portion including a distal leg, a proximal leg, and a base interconnecting the distal and proximal legs, (b) anvil means mounted on the distal leg of the U, and (c) cartridge holder means disposed in the U for linear reciprocal motion toward and away from the anvil means, a cartridge comprising:
means for cooperating with the cartridge holder means for allowing the cartridge to be removably inserted in the cartridge holder means along a first axis transverse to the axis of reciprocation of the cartridge holder means and in a direction along said first axis toward the base of the U; and
first cartridge registration means for cooperating with the frame to cause the cartridge to move along a second axis transverse to the axis of reciprocation of the cartridge holder means and in a direction along said second axis away from the base of the U to bring the cartridge into registration with the anvil means in response to reciprocation of the cartridge holder means toward the anvil means.

9. The cartridge defined in claim 8 wherein the surgical fastener applying instrument has a first cam surface on the base of the U, the first cam surface having a segment which is inclined toward the open end of the U in the direction of motion of the cartridge holder means toward the anvil means, and wherein the first cartridge registration means comprises:
first cam follower means on the cartridge means for traversing the first cam surface on the frame as the cartridge holder means moves toward the anvil means.

10. The cartridge defined in claim 9 further comprising:
stop means on the cartridge for cooperating with the cartridge holder means to force the first cam follower means into contact with the first cam surface as the cartridge holder means moves toward the anvil means.

11. The cartridge defined in claim 10 wherein the surgical fastener applying instrument has a second cam surface on the cartridge holder means and wherein the stop means comprises:
second cam follower means on the cartridge for traversing the second cam surface on the cartridge holder means as the cartridge holder means moves toward the anvil means.

12. Surgical fastener applying apparatus comprising:
a frame having a U-shaped distal portion, the U having a distal leg, a proximal leg, and a base interconnecting the distal and proximal legs;
anvil means disposed on the distal leg of the U;
cartridge holder means disposed in the U for linear reciprocal motion toward and away from the anvil means;
cartridge means;
first means associated with the cartridge holder means and the cartridge means for allowing the cartridge means to be removably inserted in the cartridge holder means along a first axis transverse to the axis of reciprocation of the cartridge holder means and in a direction along said first axis toward the base of the U in response to linear reciprocation of the cartridge holder means away from the anvil means; and
cartridge registration means associated with the frame and the cartridge means for causing the cartridge means to move along a second axis transverse to the axis of reciprocation of the cartridge holder means and in a direction along said second axis away from the base of the U to bring the cartridge means into registration with the anvil means in response to reciprocation of the cartridge holder means toward the anvil means.

13. The apparatus defined in claim 12, wherein the cartridge registration means comprises:
cam surface means on the frame including a cam surface segment which is transverse to the base of the U; and
cam follower means on the cartridge means in contact with the cam surface means.

14. The apparatus defined in claim 13 wherein the cam surface segment is inclined toward the open end of the U in the direction of motion of the cartridge holder means toward the anvil means.

15. The apparatus defined in claim 14 further comprising:
stop means associated with the cartridge holder means and the cartridge means for forcing the cam follower means into contact with the cam surface means as the cartridge holder means moves toward the anvil means.

16. The apparatus defined in claim 15 wherein the stop means comprises:
a second cam surface means on one of the cartridge holder means and the cartridge means; and
a second cam follower means on the other of the cartridge holder means and the cartridge means for contacting the second cam surface means.

17. The apparatus defined in claim 16 wherein the second cam surface means includes a second cam surface segment substantially parallel to the axis of reciprocation of the cartridge holder means.

18. The apparatus defined in claim 16 wherein the second cam surface means includes a second cam surface segment that is inclined toward the open end of the U in the direction of motion of the cartridge holder means toward the anvil means.

19. The apparatus defined in claim 16 wherein the cam surface means and cam follower means are adjacent the base of the U, and wherein the second cam surface means and cam follower means are adjacent the open end of the U.

* * * * *